US011590161B2

(12) United States Patent
Taglienti et al.

(10) Patent No.: US 11,590,161 B2
(45) Date of Patent: *Feb. 28, 2023

(54) THERAPEUTIC COMPOSITION AND METHODS

(71) Applicant: Viscera Labs, Inc., Parsippany, NJ (US)

(72) Inventors: Stephen Taglienti, Ledgewood, NJ (US); Steven L. Petruccelli, Watchung, NJ (US)

(73) Assignee: Viscera Labs, Inc., Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/788,563

(22) Filed: Feb. 12, 2020

(65) Prior Publication Data

US 2020/0179292 A1 Jun. 11, 2020

Related U.S. Application Data

(63) Continuation-in-part of application No. 16/537,823, filed on Aug. 12, 2019.

(60) Provisional application No. 62/718,055, filed on Aug. 13, 2018, provisional application No. 62/736,715, filed on Sep. 26, 2018, provisional application No. 62/804,312, filed on Feb. 12, 2019.

(51) Int. Cl.
| | | |
|---|---|---|
| *A61K 31/785* | (2006.01) | |
| *A61K 9/00* | (2006.01) | |
| *A61K 9/20* | (2006.01) | |
| *A61K 9/28* | (2006.01) | |
| *A61K 45/06* | (2006.01) | |
| *A61P 1/12* | (2006.01) | |
| *A61P 1/16* | (2006.01) | |

(52) U.S. Cl.
CPC .......... *A61K 31/785* (2013.01); *A61K 9/0053* (2013.01); *A61K 9/2009* (2013.01); *A61K 9/2013* (2013.01); *A61K 9/2054* (2013.01); *A61K 9/282* (2013.01); *A61K 9/2866* (2013.01); *A61K 45/06* (2013.01); *A61P 1/12* (2018.01); *A61P 1/16* (2018.01)

(58) Field of Classification Search
None
See application file for complete search history.

(56) References Cited

U.S. PATENT DOCUMENTS

| | | | |
|---|---|---|---|
| 5,482,718 A | 1/1996 | Shah et al. | |
| 6,506,407 B2 | 1/2003 | Watannabe et al. | |
| 7,138,143 B1 | 11/2006 | Mukai et al. | |
| 7,887,852 B2 | 2/2011 | Udell | |
| 7,939,061 B2 | 5/2011 | Prakash et al. | |
| 8,119,125 B2 | 2/2012 | Gass | |
| 8,834,858 B2 | 9/2014 | Ledwidge et al. | |
| 8,932,578 B2 | 1/2015 | Prakash et al. | |
| 9,034,883 B2 | 5/2015 | Klein et al. | |
| 9,040,483 B2 | 5/2015 | Glidden et al. | |
| 9,089,525 B1 | 7/2015 | Ling et al. | |
| 9,115,133 B2 | 8/2015 | Barawkar et al. | |
| 9,273,107 B2 | 3/2016 | Ling et al. | |
| 9,290,517 B2 | 3/2016 | Apgar et al. | |
| 9,290,557 B2 | 3/2016 | Ling et al. | |
| 9,345,715 B2 | 5/2016 | Young et al. | |
| 9,381,198 B2 | 7/2016 | Glidden et al. | |
| 9,382,243 B2 | 7/2016 | Apgar et al. | |
| 9,527,839 B2 | 12/2016 | Apgar et al. | |
| 9,527,875 B2 | 12/2016 | Hagmann et al. | |
| 9,540,364 B2 | 1/2017 | Apgar et al. | |
| 9,556,193 B2 | 1/2017 | Apgar et al. | |
| 9,580,483 B2 | 2/2017 | Ling et al. | |
| 9,637,729 B2 | 5/2017 | Prakash et al. | |
| 9,642,809 B2 | 5/2017 | Hemmingsen et al. | |
| 9,670,260 B2 | 6/2017 | Ling et al. | |
| 9,750,698 B2 | 9/2017 | Glidden et al. | |
| 9,751,924 B2 | 9/2017 | Ling et al. | |
| 9,834,563 B2 | 12/2017 | Hagmann et al. | |
| 9,834,586 B2 | 12/2017 | Lindhout et al. | |
| 9,868,733 B2 | 1/2018 | Apgar et al. | |
| 9,878,008 B2 | 1/2018 | Ling et al. | |
| 9,878,009 B2 | 1/2018 | Ling et al. | |
| 9,889,177 B2 | 2/2018 | Ling et al. | |
| 9,889,178 B2 | 2/2018 | Ling et al. | |
| 9,895,416 B2 | 2/2018 | Ling et al. | |
| 9,920,118 B2 | 3/2018 | Shen et al. | |
| 9,925,242 B2 | 3/2018 | Ling et al. | |
| 9,932,311 B2 | 4/2018 | Biftu et al. | |
| 9,957,219 B2 | 5/2018 | Bara et al. | |
| 9,963,494 B2 | 5/2018 | Ling et al. | |
| 9,974,833 B2 | 5/2018 | Ling et al. | |
| 10,786,529 B2 * | 9/2020 | Gillberg | A61K 9/4891 |
| 2003/0104052 A1 | 6/2003 | Berner et al. | |
| 2003/0124088 A1 | 7/2003 | Musuda et al. | |

(Continued)

FOREIGN PATENT DOCUMENTS

| | | |
|---|---|---|
| WO | 2007111945 A2 | 10/2007 |
| WO | 2017205684 A1 | 11/2017 |

OTHER PUBLICATIONS

Product Monograph—LODALIS, obtained from the webstie: https://pdf.hres.ca/dpd_pm/00027744.PDF (dated Oct. 2014).*
Camilleri, M. Bile, Acid Diarrhea: Prevalence, Pathogenesis, and Therapy, Gut Liver, May 2015:9(3): 332-339.
Camilleri, M., Advances in understanding of bile acid diarrhea. Expert Rev. Gastroenterol Hepotal. Jan. 2014: 8(1): 49-61.
Camilleri, M., et al., Effect of colesevelam on faecal bile acids and bowel functions in diarrhoea-predominant irritable bowel syndrome. Aliment Pharmacol Ther. Mar. 2015;41(5): 438-48.
Hegade, VS, et al., A systematic approach to the management of cholestatic pruritus in primary biliary cirrhosis. Frontlline Gastroenterology 2016; 7:158-166.

(Continued)

*Primary Examiner* — Sin J Lee

(57) ABSTRACT

In exemplary embodiments, the disclosure provides a Colesevelam Colon Specific Drug Delivery System for use in treatment of, for example, cholestasis and/or cholestatic pruritus.

24 Claims, No Drawings

(56) References Cited

U.S. PATENT DOCUMENTS

| | | |
|---|---|---|
| 2005/0249803 A1 | 11/2005 | Udell |
| 2006/0223838 A1 | 10/2006 | Jiang et al. |
| 2006/0275249 A1 | 12/2006 | Jones |
| 2007/0098678 A1 | 5/2007 | Bhagat et al. |
| 2008/0260818 A1 | 10/2008 | Penhasi et al. |
| 2009/0312358 A1 | 12/2009 | Siddlqi |
| 2009/0324710 A1 | 12/2009 | Glidden et al. |
| 2010/0008988 A1* | 1/2010 | Mehta .................. A61K 9/2866 424/474 |
| 2010/0272671 A1 | 10/2010 | Jones |
| 2010/0310607 A1* | 12/2010 | Ju ............................ A61P 7/00 424/400 |
| 2011/0038829 A1 | 2/2011 | Camilleri |
| 2011/0158932 A1 | 6/2011 | Jiang et al. |
| 2012/0177591 A1 | 7/2012 | Jones |
| 2013/0236541 A1 | 9/2013 | Gillberg et al. |
| 2014/0186288 A1 | 7/2014 | Jones |
| 2015/0031637 A1 | 1/2015 | Gillberg et al. |
| 2015/0119345 A1 | 4/2015 | Gedulin et al. |
| 2016/0051576 A1 | 2/2016 | Kopping et al. |
| 2016/0168222 A1 | 6/2016 | Ling et al. |
| 2016/0257652 A1 | 9/2016 | Biftu et al. |
| 2016/0332968 A1 | 11/2016 | Chobanian et al. |
| 2016/0338995 A1 | 11/2016 | Zhi |
| 2017/0007631 A1 | 1/2017 | Fayad et al. |
| 2017/0035784 A1 | 2/2017 | Lancaster et al. |
| 2017/0081287 A1 | 3/2017 | Biftu et al. |
| 2017/0182115 A1 | 6/2017 | Gillberg et al. |
| 2017/0182123 A1 | 6/2017 | Ling et al. |
| 2017/0210727 A1 | 7/2017 | Chen et al. |
| 2017/0217920 A1 | 8/2017 | Chobanian et al. |
| 2017/0217942 A1 | 8/2017 | Chobanian et al. |
| 2017/0232067 A1 | 8/2017 | Lindhout et al. |
| 2017/0258825 A1 | 9/2017 | Connor et al. |
| 2018/0110834 A1 | 4/2018 | Depaoli et al. |
| 2018/0134761 A1 | 5/2018 | Lindout et al. |
| 2018/0153810 A1 | 6/2018 | Glidden et al. |

OTHER PUBLICATIONS

Kuiper EM, et al., the potent bile acid sequestrant colesevelam is not effective in cholestatic pruritus: results of a double-blind, randomized, placebo-controlled trial. Hepatology, Oct. 2010; 52(4):1334-40.

Amidon, S. et al, Colon-Targeted Oral Drug Delivery Systems: Design Trends and Approaches, AAPS PharmSciTech, Aug. 2015;16(4): 731-741.

International Search Report for PCTUS21/17166 dated Jun. 24, 2021.

* cited by examiner

THERAPEUTIC COMPOSITION AND METHODS

This application is a continuation in part of U.S. Ser. No. 16/537,823 filed Aug. 12, 2019, which claims benefit under 35 USC § 119(e) to U.S. Ser. No. 62/718,055 filed Aug. 13, 2018; to U.S. Ser. No. 62/736,715 filed Sep. 26, 2018; and to U.S. Ser. No. 62/804,312 filed Feb. 12, 2019, the entireties of which are incorporated by reference herein.

SPECIFICATION

Background

Bile acids, steroid acids that are found predominantly in the bile of mammals, regulate cholesterol, triglyceride, glucose and energy homeostasis, and facilitate digestion and absorption of lipids in the small intestine. Emulsification of lipids and fat-soluble vitamins in the intestine allows the formation of micelles that can then be transported via the lacteal system. Other functions of bile acids include driving the flow of bile to eliminate catabolites from the liver and aiding in the reduction of the bacteria flora found in the small intestine and biliary tract. Bile acids are also involved in the regulation of their own synthesis and enterohepatic circulation. See, e.g., Staels et al., Diabetes Care (2009) vol. 32 no. suppl 2 S237-S245.

In humans, bile acid production occurs primarily in the perivenous hepatocytes through a series of enzymatic reactions that convert cholesterol into the two primary bile acids, cholic acid and chenodeoxycholic acid. The primary bile acids are synthesized by two distinct pathways. In the "classic" or "neutral" pathway, the primary bile acids are produced by hydroxylation of cholesterol through catalysis by the cytochrome P450 enzyme cholesterol 7alpha-hydroxylase (cyp7a1), which catalyzes the first and rate-limiting step in the classical bile acid synthesis pathway. (See, e.g., Inagaki et al., Cell Metabolism 2:217-25 (October 2005)).

Bile acids synthesized in the liver are immediately secreted into bile, reabsorbed in the intestine and transported back to the liver. The enterohepatic circulation of bile acids is very efficient in humans. Small amounts of bile acids may spill over into the systemic circulation, reabsorbed when passing through the renal tubules in the kidney, and are then circulated back to the liver through systemic circulation. Some bile acids secreted in the bile duct are reabsorbed in the cholangiocytes (bile duct epithelial cells) and recycled back to hepatocytes (the cholangiohepatic shunt). Bile acids are stored in the gallbladder. After each meal, cholecystokinin secreted from the intestine stimulates gallbladder contraction to empty bile acids into the intestinal tract. When passing down the intestinal tract, small amounts of unconjugated bile acids are reabsorbed in the upper intestine by passive diffusion. Most bile acids (95%) are reabsorbed in the brush border membrane of the terminal ileum, transdiffused across the enterocyte to the basolateral membrane, and secreted into portal blood circulation to liver sinusoids and are taken up into hepatocytes. DCA is reabsorbed in the colon and recycled with CA and CDCA to the liver. A bile acid pool of ~3 g consisting of ~40% CA, 40% CDCA, 20% DCA, and trace amount of LCA, is recycled 4 to 12 times a day. Bile acids lost in the feces (~0.5 g/day) are replenished by de novo synthesis in the liver to maintain a constant bile acid pool. (See Chiang J Y. Bile acid metabolism and signaling. Compr. Physiol. 2013 July; 3(3):1191-212).

When cholic acid and chenodeoxycholic acid are secreted into the lumen of the intestine, intestinal bacteria dehydroxylate a portion of each to form the secondary bile acids, deoxycholic acid (derived from cholic acid) and lithocholic acid (derived from chenodeoxycholic acid). Hepatic cells may conjugate these four bile with one of two amino acids, glycine or taurine, to form a total of eight possible conjugated bile acids, referred to as bile salts. Thus, in total the principal bile acids are cholic acid, chenodeoxycholic acid, glycocholic acid, taurocholic acid, deoxycholic acid and lithocholic acid. All four of these bile acids can be transported back into the blood stream, be returned to the liver, and be re-secreted through enterohepatic circulation. (See, e.g., Staels et al., Diabetes Care (2009) vol. 32 suppl 2 S237-S245).

The primary bile acids (cholic acid and chenodeoxycholic acid) are synthesized in the liver), while the secondary bile acids (deoxycholic acid and lithocholic acid) are made by bacteria. The four bile acids are secreted into the bile canalicular lumen for storage in the gallbladder as mixed micelles with phospholipids and cholesterol. Upon ingestion of a meal, cholecystokinin stimulates gallbladder contraction resulting in its release of micellar bile acids into the intestinal lumen to aid digestion. Enterohepatic circulation enables about 90-95% of bile acids to be reabsorbed from the distal ileum and transported back to the liver; this bile acid uptake and transportation occurs primarily by pericentral hepatocytes. The approximately 5% of bile acids that are not reabsorbed are eliminated in the feces, and that amount of loss is subsequently replaced by de novo bile acid synthesis in the liver. See, e.g., Rose et al., Cell Metabolism, 14:1, pp 123-130 (6 Jul. 2011).

As described herein, abnormal bile acid homeostasis can result in, or exacerbate, a number of disorders, including cholestasis, portosystemic shunt, Crohn's disease, hepatic microvascular dysplasia, inflammatory bowel diseases (IBD), irritable bowel syndrome, colonic cancer, cholestasis, cholestatic pruritus, insufficient control of blood glucose, and cardiovascular disease, such as hypercholesterolemia. In addition, bile acids play a role in modulating the metabolic syndrome, a cluster of cardiovascular disease risk factors that include visceral obesity, insulin resistance, dyslipidemia, increased blood pressure, and hypercoagulability. Thus, modulation of bile acid activity can provide a number of beneficial therapeutic effects. Current approaches to disease management include: Low fat diet, oral bile acid binders (cholestyramine, colestipol, colesevelam), Cholestyramine treatment is by far the most studied of the existing agents, Colesevelam binds bile acids with a higher affinity than cholestyramine or colestipol; one study found it to be effective in patients who had failed treatment with cholestyramine.

The major goal of any drug delivery system is to supply a therapeutic amount of drug to a target site in a body, so that the desired drug concentration can be achieved swiftly and then maintained. Targeted drug delivery implies selective and effective localization of drug into the target at therapeutic concentrations with limited access to non-target sites. A targeted drug delivery system is preferred in drugs having instability, low solubility and short half-life, large volume of distribution, poor absorption, low specificity and low therapeutic index. Targeted drug delivery may provide maximum therapeutic activity by preventing degradation or inactivation of drug during transit to the target site. Meanwhile, it can also minimize adverse effects because of inappropriate disposition and minimize toxicity of potent drugs by reducing dose. An ideal targeted delivery system should be nontoxic, biocompatible, and biodegradable and physicochemically stable in vivo and in vitro. The preparation of the delivery system must be reasonably simple, reproducible and cost-effective. The targeted drug delivery is dependent on the identification and exploitation of a attribute that is specific to the target organ. A Colon Specific Drug Delivery System (CSDDS) is beneficial for the localized treatment of several diseases, for example, mainly inflammatory bowel diseases (IBD), irritable bowel syndrome, colonic cancer, cholestasis, cholestatic pruritus, insufficient control of blood glucose, and cardiovascular disease, such as hypercholesterolemia. An aim of the invention is to achieve a clinically CSDDS relevant bioavailability of poorly absorbed drugs from the upper parts of the gastrointestinal tract because of their polar nature and/or vulnerability to chemical and enzymatic degradation in the small intestine specifically for proteins and peptides. The colonic drug delivery provide more effective therapy of diseases such as, for example, inflammatory bowel diseases (IBD), irritable bowel syndrome, colonic cancer, cholestasis, cholestatic pruritus, insufficient control of blood glucose, and cardiovascular disease, such as hypercholesterolemia, and also has potential to deliver macromolecular drugs orally. Colon related pathologies range in seriousness from constipation and diarrhea to the incapacitating inflammatory bowel diseases through to colon cancer, the third most widespread form of cancer in both women and men.

Lipids constitute a broad group of naturally occurring hydrophobic or amphiphilic molecules that include fatty acids, glycerolipids, glycerophospholipids, sphingolipids, saccharolipids, and polyketides, sterol lipids and prenol lipids. The main biological functions of lipids include energy storage, as structural components of cell membranes, and as important signaling molecules. Given these fundamental roles, all cells use and rely on lipids. One process used to transport lipids to cells involves apolipoproteins. Apolipoproteins are proteins that bind to lipids to form lipoproteins, which are the vehicles used for transporting the lipids, including triglycerides and cholesterol, through the lymphatic and circulatory systems. The lipid components of lipoproteins are not themselves soluble in water. However, because of their amphipathic properties, apolipoproteins and other amphipathic molecules (such as, e.g., phospholipids) can surround the lipids, creating the lipoprotein particle that is itself water-soluble, and can thus be carried through water-based circulation, i.e., blood and lymph, etc.

There five major groups of lipoprotein particles, and the lipoprotein density and type of apolipoproteins it contains determines the fate of the particle and its influence on metabolism. Chylomicrons are the largest lipoprotein particle and these particles carry triglycerides from the intestines to the liver, skeletal muscle, and adipose tissue. Very low-density lipoprotein (VLDL) particles are large, triglyceride-rich lipoprotein secreted by the liver that transports triglycerides to adipose tissue and muscle. The third group lipoprotein particles are intermediate-density lipoprotein (IDL) particles, an intermediate between VLDL and low-density lipoprotein (LDL). IDL particles are formed when lipoprotein lipase removes triglycerides from VLDL particles in the capillaries and the return these smaller particles to the circulation. The IDL particles have lost most of their triglyceride, but they retain cholesteryl esters. Some of the IDL particles are rapidly taken up by the liver; others remain in circulation, where they undergo further triglyceride hydrolysis and are converted to LDL. LDL particles carry cholesterol from the liver to cells of the body, where these particles bind to LDL receptors that are subsequently endocytosed in vesicles form via clathrin-coated pits. After the clathrin coat is shed, the vesicles ultimately deliver the LDL to lysosomes where the cholesterol esters are hydrolyzed. The last group of lipoprotein particles is high-density lipoprotein (HDL) particles, which collect cholesterol from the body's tissues and bring it back to the liver.

High levels of lipids, e.g., cholesterol, and/or lipoprotein particles, e.g., VLDL, IDL, and/or LDL can have deleterious effects on the cardiovascular system. For example, as a major extracellular carrier of cholesterol, LDL plays important physiologic roles in cellular function and regulation of metabolic pathways. Cells have complex feedback mechanisms that ensure sufficient supply of cholesterol and prevent its excessive accumulation in the blood. However, under pathologic conditions of, e.g., hyperlipidemia, oxidative stress and/or genetic disorders, specific components of LDL become oxidized or otherwise modified, with a consequence that cholesterol transport by such modified LDL is diverted from its physiologic targets and accumulates in the blood.

One effect of this accumulation is the high amounts of cholesterol and/or LDL become embedded in the walls of blood vessels, an in so doing invokes an inflammatory response. In response to this inflammation, blood monocytes adhere to the endothelium, transmigrate into the subendothelial space, and differentiate toward macrophages. Macrophages, in turn, engulf the cholesterol deposits and modified LDL by phagocytosis via scavenger receptors, which are distinct from LDL receptors. However, the adaptive mechanisms mediated by macrophages are not sufficient to process the uncontrolled cholesterol and/or LDL deposition seen under pathologic conditions. As a result, the lipid-laden macrophages transform into "foam cells" or "foamy cells" having a M1 phenotype. Both cholesterol/LDL deposition and the attendant foam cell-mediated pro-inflammatory reactions in the blood wall lead to the development of atherosclerotic lesions. Left untreated, this lipid accumulation and pro-inflammatory response result in the progression of the lesions, which eventually leads to a cardiovascular disease.

Another effect of high cholesterol/LDL accumulation in the blood is the formation LDL aggregates or LDL agglomerates. Being of high molecular weight, LDL agglomerates initiate an inflammatory response in a manner similar to that invoked by pathogens like viruses or bacteria. The inflammatory response triggers agglomerate uptake by macrophages which converts these cells into foam cells having a M1 phenotype, and the release of inflammation inducing molecules. Once again, left untreated, the lipid accumulation and pro-inflammatory response can result in a cardiovascular disease.

Other drugs are known to lower serum concentrations of LDL cholesterol and may help prevent formation, slow progression, and cause regression of atherosclerotic lesions. Further, trials of these lipid-regulating drugs have shown an association between increases in HDL cholesterol and reduction in clinical coronary events. For example, HMG-CoA reductase inhibitors, otherwise known as "statins," inhibit the enzyme that catalyzes the rate-limiting step in cholesterol syntesis. Statins are more effective than other drugs in lowering plasma concentrations of LDL cholesterol, increasing HDL cholesterol by up to about 15% with high doses, and reducing levels of triglyceride. Statins lower LDL cholesterol levels in the bloodstream by indirectly increasing the number of LDL receptors on the surface of cells. Despite the success of statins, there is a significant patient population, particularly those individuals having substantially elevated blood cholesterol levels, for which these drugs alone are insufficient to achieve the desired efficacy. Moreover, because statins are not able to mobilize cholesterol sequestered in tissue and/or cells (e.g., foam cells in atherosclerotic plaques), this class of compounds, alone, cannot prevent the development of atherosclerosis.

Bile acid sequestrants are another lipid regulating drug that may lower LDL-cholesterol by about 10 to 20 percent. Cholestyramine, colestipol, and colesevelam are the three main bile acid sequestrants currently available. Small doses of sequestrants can produce useful reductions in LDL-cholesterol. These drugs also tend to increase HDL cholesterol and, in patients with hypertriglyceridemia, cholestyramine, colestipol and, to a lesser extent, colesevelam raise plasma triglycerides. When these drugs are combined, their effects are added together to lower LDL-cholesterol by over 40 percent.

Attempts to treat cardiovascular disease by controlling levels of lipids and/or lipoproteins in the blood have met with limited success. For example, although administration of statins reduces cardiovascular risk in some individuals, these therapeutic compounds do not reduce triglyceride levels. Thus, in individuals at cardiovascular risk who exhibit deleteriously high levels of triglycerides, another class of therapeutic compounds called fibrates may be administered. However, although lowering triglyceride and LDL levels, fibrates do not affect the level of HDL, the lipoprotein particle known to be protective against cardiovascular disease. Lastly, combination treatments involving statins and fibrates, while effective, cause a significant increase to the risk of myopathy and rhabdomyolysis, and therefore can only be carried out under very close medical supervision. In view of these problems, there is, therefore, clearly a need for improved compounds and compositions for the use and treatment of cardiovascular diseases, including those associated with high lipid and/or lipoprotein levels. The present specification discloses pharmaceutical compositions and methods for treating an individual suffering from a cardiovascular disease.

Diabetes mellitus refers to a group of metabolic diseases in which patients have high blood sugar level. It is a major public health problem due to high number of affected patients since 171 million people worldwide corresponding to 2.8% of the population in 2000 are diabetic. Diabetes is now considered as epidemic: the number of patients should almost double by 2030. There are mainly two types of diabetes. Type 1 diabetes is mainly characterized by insulin dependent patients, is known to be autoimmune, sometimes triggered by infection factors. It usually starts in patients younger than 30 and it accounts about 5-10% of all cases of diabetes. Type 2 diabetes, mainly characterized by insulin independence, has a later onset than type 1 diabetes and is therefore named adult-onset diabetes. It accounts for about 90-95% of all diabetes cases. Many factors can potentially give rise to, or exacerbate type 2 diabetes. These include hypertension, elevated cholesterol, metabolic syndrome and overweight/obesity. As an example, approximately 90% of patients with type 2 diabetes are overweight/obese. Other forms of diabetes include gestational diabetes, congenital diabetes, cystic fibrosis-related diabetes, steroid diabetes, and several forms of monogenic diabetes. Current treatments consist in insulin administration for type 1 diabetes and/or glucose-lowering medications or insulin sensitizers for type 2 diabetes. Insulin is a hormone involved in the glucose homeostasis, together with glucagon. In response to rising levels of blood glucose, insulin is produced by pancreatic beta cells located in the islets of Langerhans. Thus, glucose is taken up from the blood by hepatocytes, muscle cells, and adipocytes used either as energy source or for storage as glycogen and triglycerides. It also inhibits lipolysis, preventing fatty acid release from fat tissues. On the contrary, low blood glucose levels result both in a reduced production and release of insulin. Together with glucagon action, it results in glucose release into blood stream. In pathological situations, either insulin production by beta-cells is not sufficient (type 1 diabetes) and/or cells poorly respond to it (insulin resistance; type 2 diabetes), leading to persistent high levels of blood glucose. Precise mechanisms involved in these pathologies are not yet completely understood.

Decrease in insulin production characterizing type 1 diabetes is due to a destruction of beta-cells by an autoimmune process that consists in autoantibodies production, activation of self-reactive lymphocytes and infiltration of pancreas to destroy beta-cells. Type 2 diabetes mellitus is considered as a complex metabolic disorder. It results from the combination of impaired pancreatic insulin secretion due to beta-cells dysfunction, insulin resistance as well as damaged glucagon secretion Impairment of glucose-stimulated production of insulin involves progressive loss of pancreatic beta-cells as well as a decline in islet cells function. Insulin resistance consists for example in suppressed or reduced effects of insulin in peripheral organs/tissues (liver, muscles and fat tissues) or enhanced lipolysis in adipocytes leading to increased circulation of free fatty acids. Those events result in increased endogenous glucose production by the liver together with decreased glucose uptake due to reduced insulin receptor expression, defects in post-receptor actions of insulin, hepatic glucose overproduction or blocking of insulin-signaling pathways. Insulin resistance is a hallmark of a more complex syndrome, named metabolic syndrome that is a grouping of risk factors for coronary heart disease and diabetes mellitus including abdominal obesity, elevated triglyceride levels, decreased high-density lipoprotein levels, elevated blood pressure, and elevated fasting plasma glucose levels. 75% of type 2 diabetes patients have metabolic syndrome.

Persistent high blood glucose leads both to acute and chronic complications that may be very disabling, even fatal for diabetic patients such as heart disease and stroke that are the most life-threatening consequences of diabetes mellitus. Long-term persistent elevated blood glucose damages blood vessels, leading to microvascular and macrovascular angiopathy which account for most of the increased morbidity and mortality associated with the disease. Microvascular complications are responsible of diabetic cardiomyopathy, nephropathy both sometimes leading to organ failure, retinopathy which can lead to severe vision loss and neuropathy. Macrovascular complications rather concerns cardiovascular impairments that are responsible of coronary artery disease that in the end provokes angina or myocardial infarction, diabetic myonecrosis, peripheral vascular disease and stroke. Macrovascular complications are more common and up to 80% of patients with type 2 diabetes will develop or die of a macrovascular disease.

Unfortunately, existing treatments do not succeed in restoring normoglycaemia in the long term, since beta-cell function declines over time. Moreover, there is presently no single drug able to reverse all aspects of the disease.

Control of glycaemia in type 1 diabetes is almost exclusively achieved with injections of exogenous insulin, since patients no longer produce insulin. Insulin may also be administered in type 2 diabetes patients, when glucose-lowering drugs and diet fail to control glycaemia. It is nowadays more frequently administered to these patients, since it delays development and progression of complications. Use of insulin, however, comprises side effects including hypoglycaemia when dosage is not appropriate, increased risk of developing colorectal cancer and gaining weight, which is not recommended for diabetic patients, particularly obese ones.

The progressive nature of type 2 diabetes implies that many patients will eventually require a combination of antidiabetics, possibly together with insulin. Antidiabetics have been developed in order to counteract the main mechanisms involved in type 2 diabetes: insulin resistance (biguanides and thiazolidinediones) and insulin secretion (sulfonylureas, glinides, dipeptidylpeptidase-4 inhibitors, glucagon-like peptide 1 receptor agonists), in addition to particular mechanisms dealing with delayed absorption of glucose by gastrointestinal tract. However, most of these medications have been shown to have deleterious side effects such as weight gain, peripheral edema or congestive heart failure and to loss in efficiency in a long term use.

Despite the increasing number of therapeutic options related to diabetes, none is able to reverse all the aspects of the disease including progressive loss of beta cells function and the management of all the complications. Thus, there is a need for alternative and improved medications for the treatment of diabetes and related conditions.

Pruritus, or itch, is a sensation that stimulates the desire or reflex to scratch, which can be either generalized or localized. The cause of pruritus is not fully understood. Proposed contributors to the pathogenesis of pruritus may include anemia or other manifestation of erythropoietin deficiency, histamine release from skin mast cells, skin dryness, secondary hyperparathyroidism, hyperphosphatemia with increased calcium phosphate deposition in the skin and alterations in the endogenous opioidergic system with overexpression of opioid mu-receptors. Chronic pruritus can seriously diminish the quality of life in its sufferers as it can be intractable and incapacitating. It is a seriously debilitating condition, comparable to chronic pain, which can lead to frustration, desperation and depression. Moreover, chronic scratching often produces open skin lesions, subject to primary or secondary infection, scarring and potential disfigurement. Chronic pruritus is often an indication of underlying disease and is always present in diseases such as urticaria and atopic dermatitis. Diagnosis of the underlying disease is desirable and clinical presentation, patient history, and patient self-evaluation form important parts of such diagnosis. Pruritus is a well-known, frequent and distressing symptom of cholestasis. In clinical practice, the most commonly encountered cholestatic liver diseases (CLD) associated with pruritus are primary biliary cirrhosis (PBC), primary sclerosing cholangitis (PSC) and intrahepatic cholestasis of pregnancy. Cholestatic liver diseases, or cholestasis, are a group of disorders of varying causes that result when bile flow is impaired. Cholestasis can cause progressive liver damage and eventually lead to end-stage liver disease. The mechanisms by which the liver is injured and fibrosis is stimulated in cholestatic liver disease are unclear.

In exemplary embodiments, the invention provides a Colesevelam Colon Specific Drug Delivery System for use in treatment of, for example, cholestasis and/or cholestatic pruritus.

In exemplary embodiments, the invention provides a Colesevelam Colon Specific Drug Delivery System for use in treatment of, for example, inflammatory bowel diseases (IBD), irritable bowel syndrome, colonic cancer, cholestasis, cholestatic pruritus, insufficient control of blood glucose, and cardiovascular disease, such as hypercholesterolemia.

All references cited herein are incorporated herein by reference in their entireties.

BRIEF SUMMARY

The disclosure provides an oral drug delivery system comprising: a) a core comprising a therapeutically effective amount of at least one active agent present in an amount of from about about 35% to about 65% w/w of the core, and a drug release controlling component capable of providing release of the active agent primarily in a region selected from the group consisting of the lower gastrointestinal tract, the large intestine, the jejunum, the ileum, the cecum, the colon, the rectum, and combinations thereof, b) an outer coating encasing the core, and optionally a plasticizer, wherein after ingestion by a patient the active agent is released primarily in the region selected from the group consisting of the lower gastrointestinal tract, the large intestine, the jejunum, the ileum, the cecum, the colon, the rectum, and combinations thereof. The disclosure provides an oral drug delivery system wherein the at least one active agent is selected from the group consisting of colesevelam, pharmaceutically acceptable salts thereof, derivatives thereof, and combinations thereof. The disclosure provides an oral drug delivery system wherein the at least one active agent is present in an amount selected from the group consisting of about 250 mg, about 500 mg, about 625 mg, and about 650 mg. The disclosure provides an oral drug delivery system wherein the at least one active agent is present in an amount of about 250 to about 650 mg. The disclosure provides an oral drug delivery system wherein the therapeutically effective amount of the at least one active agent is present in an amount of from about 50% to about 64% w/w of the core. The disclosure provides an oral drug delivery system wherein the therapeutically effective amount of the at least one active agent is present in an amount of about 63.13% w/w of the core. The disclosure provides an oral drug delivery system wherein the oral drug delivery system releases the active agent primarily in the lower gastrointestinal tract. The disclosure provides an oral drug delivery system wherein about 80% to about 100% w/w of the at least one active agent is released in the lower gastrointestinal tract. The disclosure provides an oral drug delivery system wherein about 100% w/w of the at least one active agent is released in the lower gastrointestinal tract. The disclosure provides an oral drug delivery system wherein the oral drug delivery system releases the active agent primarily in the large intestine. The disclosure provides an oral drug delivery system wherein about 80% to about 100% w/w of the at least one active agent is released in the large intestine. The disclosure provides an oral drug delivery system wherein about 100% w/w of the at least one active agent is released in the large intestine. The disclosure provides an oral drug delivery system wherein the oral drug delivery system releases the active agent primarily in the colon. The disclosure provides an oral drug delivery system wherein about 80% to about 100% w/w of the at least one active agent is released in the colon. The disclosure provides an oral drug delivery system wherein about 100% w/w of the at least one active agent is released in the colon. The disclosure provides an oral drug delivery system wherein the drug release controlling component capable of providing release of the active agent primarily in a region selected from the group consisting of the lower gastrointestinal tract, the large intestine, the jejunum, the ileum, the cecum, the colon, the rectum, and combinations thereof is at least one erodible matrix material. The disclosure provides an oral drug delivery system wherein the at least one erodible matrix material is selected from the group consisting of microcrystalline cellulose, hydroxypropyl methyl cellulose (HPMC), HPMCP, HPMCAS, hydroxypropyl methyl cellulose acetate trimellitate (HPMCAT), ethylhydroxy ethylcellulose (EHEC), and combinations thereof. The disclosure provides an oral drug delivery system wherein the at least one erodible matrix material is present in a concentration of about 20% to about 40% w/w of the core. The disclosure provides an oral drug delivery system wherein the at least one erodible matrix material is present in a concentration of about 5% to about 15% w/w of the core. The disclosure provides an oral drug delivery system wherein the at least one erodible matrix material is present in a concentration of about 8% to about 13% w/w of the core. The disclosure provides an oral drug delivery system wherein the at least one erodible matrix material is present in a concentration of about 12.12% w/w of the core. The disclosure provides an oral drug delivery system wherein the erodible matrix material is microcrystalline cellulose. The disclosure provides an oral drug delivery system wherein the erodible matrix material is a combination if microcrystalline cellulose and hydroxypropyl methyl cellulose (HPMC). The disclosure provides an oral drug delivery system wherein the core further comprises at least one of the following excipients: diluent, binding agent, lubricant, disintegrant, stabilizer, and combinations thereof. The disclosure provides an oral drug delivery system wherein the core comprises a disintegrant, wherein the disintegrant comprises colloidal silicon dioxide, in an amount of from about 0.1% to about 4% w/w of the core. The disclosure provides an oral drug delivery system wherein the core comprises a lubricant, wherein the lubricant comprises magnesium stearate, in an amount of from about 0.1% to about 4% w/w of the core. The disclosure provides an oral drug delivery system wherein the coating is an enteric coating. The disclosure provides an oral drug delivery system wherein the coating allows the at least one active agent formulation to pass through the stomach substantially intact and subsequently disintegrate substantially in the large intestine of a patient. The disclosure provides an oral drug delivery system wherein the plasticizer is present in a concentration of about 0.5% to about 2% w/w of the outer coating. The disclosure provides an oral drug delivery system wherein the plasticizer is present in a concentration of about 0.75% to about 1% w/w of the outer coating. The disclosure provides an oral drug delivery system wherein the plasticizer is present in a concentration of about 0.87% w/w of the outer coating. The disclosure provides an oral drug delivery system wherein the plasticizer is selected from the group consisting of dibutyl sebacate, diethyl phthalate, triethyl citrate, tributyl citrate, and triacetin, acetylated monoglycerides, diacylated monoglyceride, phthalate esters, castor oil, and combinations thereof. The disclosure provides an oral drug delivery system wherein the plasticizer is diacylated monoglyceride.

The disclosure provides a method of preventing and/or treating pruritus in a patient in need thereof comprising: selecting a patient in need of preventing and/or treating pruritus; administering to the patient the oral drug delivery system of the disclosure, wherein pruritus is prevented and/or treated in the patient. The disclosure provides a method of preventing and/or treating pruritus wherein the oral drug delivery system is administered in single or divided doses of one to four times daily. The disclosure provides a method of preventing and/or treating pruritus wherein the pruritus is associated with cholestasis, cholestatic pruritus, or biliary pruritus. The disclosure provides a method of preventing and/or treating pruritus wherein the pruritus is associated with cholestatic liver disease. The disclosure provides a method of preventing and/or treating pruritus further comprising administering one or more additional antipruritic agents. The disclosure provides a method of preventing and/or treating pruritus wherein the one or more additional antipruritic agents are selected from the group consisting of antihistamines, corticosteroids, immunomodulators, immunosuppressants, antidepressants and anticonvulsants.

The disclosure provides a method of preventing and/or treating a disorder related to elevated serum cholesterol concentration in a patient in need thereof comprising: selecting a patient in need of preventing and/or treating a disorder related to elevated serum cholesterol concentration; administering to the patient the oral drug delivery system of the disclosure, wherein a disorder related to elevated serum cholesterol concentration is prevented and/or treated in the patient. The disclosure provides a method of preventing and/or treating a disorder related to elevated serum cholesterol concentration in a patient in need thereof, wherein the oral drug delivery system is administered in single or divided doses of one to four times daily. The disclosure provides a method of preventing and/or treating a disorder related to elevated serum cholesterol concentration in a patient in need thereof, further comprising administering one or more additional active agents. The disclosure provides a method of preventing and/or treating a disorder related to elevated serum cholesterol concentration in a patient in need thereof, further comprising administering one or more additional active agents selected from the group consisting of mevastatin, pravastatin, atorvastatin, rosuvastatin, cerivastatin, fluvastatin, lovastatin, and simvastatin, a fibric acid derivative, niacin, ezetimibe, probucol, raloxifene and its derivatives, and an unsaturated omega-3 fatty acid.

The disclosure provides a method of preventing and/or treating insufficient glycemic control in a patient in need thereof comprising: selecting a patient in need of preventing and/or treating insufficient glycemic control; administering to the patient the oral drug delivery system of the disclosure, wherein insufficient glycemic control is prevented and/or treated in the patient. The disclosure provides a method of preventing and/or treating insufficient glycemic control in a patient in need thereof, wherein the oral drug delivery system is administered in single or divided doses of one to four times daily. The disclosure provides a method of preventing and/or treating insufficient glycemic control in a patient in need thereof, further comprising administering one or more additional active agents. The disclosure provides a method of preventing and/or treating insufficient glycemic control in a patient in need thereof, further comprising administering one or more additional active agents selected from the group consisting of metformin, sulphonylureas, thiazolidinediones, glinides, alpha-glucosidase blockers, GLP-1 and GLP-1 analogues, and insulin and insulin analogues; for example, despite mono-therapy with metformin, a sulphonylurea, pioglitazone or (basal) insulin, or despite dual combination therapy with a metformin/pioglitazone, metformin/sulphonylurea, metformin/(basal) insulin, sulphonylurea/pioglitazone, sulphonylurea/(basal) insulin or pioglitazone/(basal) insulin combination.

The disclosure provides a method for reducing elevated low-density lipoprotein cholesterol (LDL) concentration a patient in need thereof comprising: selecting a patient in need of reducing elevated LDL concentration; administering to the patient the oral drug delivery system of the disclosure, wherein the LDL concentration is reduced in the patient. The disclosure provides a method for reducing elevated low-density lipoprotein cholesterol (LDL) concentration a patient, wherein the oral drug delivery system is administered in single or divided doses of one to four times daily. The disclosure provides a method for reducing elevated low-density lipoprotein cholesterol (LDL) concentration a patient, further comprising administering one or more additional active agents. The disclosure provides a method for reducing elevated low-density lipoprotein cholesterol (LDL) concentration a patient, further comprising administering one or more additional active agents selected from the group consisting of mevastatin, pravastatin, atorvastatin, rosuvastatin, cerivastatin, fluvastatin, lovastatin, and simvastatin, a fibric acid derivative, niacin, ezetimibe, probucol, raloxifene and its derivatives, and an unsaturated omega-3 fatty acid.

The disclosure provides a method of preventing and/or treating bile acid malabsorption diarrhea in a patient in need thereof comprising: selecting a patient in need of preventing and/or treating bile acid malabsorption diarrhea; administering to the patient the oral drug delivery system as disclosed herein, wherein bile acid malabsorption diarrhea is prevented and/or treated in the patient. The disclosure provides a wherein the oral drug delivery system is administered in single or divided doses of one to four times daily.

The disclosure provides for the use of the compositions of the disclosure for the production of a medicament for treating the indications as set forth herein. In accordance with a further embodiment, the present disclosure provides a use of the pharmaceutical compositions described above, an amount effective for use in a medicament, and most preferably for use as a medicament for treating a disease or disorder in a subject. In accordance with yet another embodiment, the present disclosure provides a use of the pharmaceutical compositions described above, and at least one additional therapeutic agent, in an amount effective for use in a medicament, and most preferably for use as a medicament for treating a disease or disorder associated with disease in a subject.

DETAILED DESCRIPTION

The disclosure relates to methods and materials for administering a bile acid sequestrant (e.g., colesevelam) to treat conditions associated with diarrhea (e.g., bile acid malabsorption induced diarrhea). For example, the disclosure provides compositions and methods for treating diarrhea, such as bile acid malabsorption diarrhea, in a mammal, including without limitation, a human, dog, cat, horse, pig, monkey, or sheep. Examples of diarrhea conditions that can be treated as described herein include, without limitation, bile acid malabsorption induced diarrhea, ileal resection diarrhea, radiation ileitis, Crohn's ileitis, acute Yersinia ileitis, diabetic diarrhea, diarrhea associated with small bowel bacterial overgrowth, irritable bowel syndrome with diarrhea, diarrhea-predominant irritable bowel syndrome, functional diarrhea, and pancreatic transplant associated diarrhea. Examples of bile acid sequestrants that can be used as described herein include, without limitation, colesevelam, cholestyramine, colestipol, and chitosan. In some cases, the methods provided herein can include identifying a mammal (e.g., human) to be treated.

As used herein the terms "Lower Gastrointestinal Tract" or "Lower GI Tract" refers to the lower part of the gastrointestinal tract that includes the jejunum and ileum of the small intestine and the large intestine. (www.ncbi.nlm.nih-.gov/pubmedhealth/PMHT0022856/). As used herein the term "Large Intestine" refers to the part of the intestine that includes the appendix, cecum, colon, and rectum. The large intestine absorbs water from stool and changes it from a liquid to a solid form. (www.ncbi.nlm.nih.gov/pubmedhealth/PMHT0022246/).

As used herein the term "active pharmaceutical ingredient" ("API") or "pharmaceutically active agent" is a drug or agent which can be employed for the compositions and methods of the disclosure and is intended to be used in the human or animal body in order to heal, to alleviate, to prevent or to diagnose diseases, ailments, physical damage or pathological symptoms; allow the state, the condition or the functions of the body or mental states to be identified; to replace active substances produced by the human or animal body, or body fluids; to defend against, to eliminate or to render innocuous pathogens, parasites or exogenous substances or to influence the state, the condition or the functions of the body or mental states. Drugs in use can be found in reference works such as, for example, the Rote Liste or the Merck Index. Examples which may be mentioned include, for example, colesevelam.

As used herein, "pharmaceutically acceptable salts" refer to derivatives of the disclosed compounds wherein the therapeutic compound is modified by making acid or base salts thereof. Examples of pharmaceutically acceptable salts include, but are not limited to, mineral or organic acid salts of the active agent. The pharmaceutically acceptable salts include the conventional non-toxic salts, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and other known to those of ordinary skill in the pharmaceutical sciences. Lists of suitable salts are found in texts such as *Remington's Pharmaceutical Sciences*, 18th Ed. (Alfonso R. Gennaro, ed.; Mack Publishing Company, Easton, Pa., 1990); *Remington: the Science and Practice of Pharmacy* 19$^{th}$ Ed. (Lippincott, Williams & Wilkins, 1995); *Handbook of Pharmaceutical Excipients*, 3$^{rd}$ Ed. (Arthur H. Kibbe, ed.; Amer. Pharmaceutical Assoc., 1999); the *Pharmaceutical Codex: Principles and Practice of Pharmaceutics* 12$^{th}$ Ed. (Walter Lund ed.; Pharmaceutical Press, London, 1994); The United States Pharmacopeia: The National Formulary (United States Pharmacopeial Convention); and *Goodman and Gilman's: the Pharmacological Basis of Therapeutics* (Louis S. Goodman and Lee E. Limbird, eds.; McGraw Hill, 1992), the disclosures of which are hereby incorporated by reference.

An amount is "effective" as used herein, when the amount provides an effect in the subject. As used herein, the term "effective amount" means an amount of a compound or composition sufficient to significantly induce a positive benefit, including independently or in combinations the benefits disclosed herein, but low enough to avoid serious side effects, i.e., to provide a reasonable benefit to risk ratio, within the scope of sound judgment of the skilled artisan. For those skilled in the art, the effective amount, as well as dosage and frequency of administration, may be determined according to their knowledge and standard methodology of merely routine experimentation based on the present disclosure.

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the terms "prevent," "preventing" and "prevention" in the context of the administration of a therapy to a subject refer to the prevention or inhibition of the recurrence, onset, and/or development of a disease or condition, or a combination of therapies (e.g., a combination of prophylactic or therapeutic agents).

As used herein, the terms "therapies" and "therapy" can refer to any method(s), composition(s), and/or agent(s) that can be used in the prevention, treatment and/or management of a disease or condition, or one or more symptoms thereof.

As used herein, the terms "treat," "treatment," and "treating" in the context of the administration of a therapy to a subject refer to the reduction or inhibition of the progression and/or duration of a disease or condition, the reduction or amelioration of the severity of a disease or condition, and/or the amelioration of one or more symptoms thereof resulting from the administration of one or more therapies.

As used herein, the term "about" when used in conjunction with a stated numerical value or range has the meaning reasonably ascribed to it by a person skilled in the art, i.e. denoting somewhat more or somewhat less than the stated value or range.

Active Agent

As set forth above, the disclosure relates to methods and materials for administering an active agent, such as a bile acid sequestrant (e.g., colesevelam) to treat conditions associated with diarrhea (e.g., bile acid malabsorption induced diarrhea). Colesevelam hydrochloride (WELCHOL) is a bile acid sequestrant indicated as an adjunct to diet and exercise to reduce elevated low-density lipoprotein cholesterol (LDL-C) in adults with primary hyperlipidemia as monotherapy or in combination with an hydroxymethyl-glutaryl-coenzyme A (HMG CoA) reductase inhibitor; reduce LDL-C levels in boys and postmenarchal girls, 10 to 17 years of age, with heterozygous familial hypercholesterolemia as monotherapy or in combination with a statin after failing an adequate trial of diet therapy; and improve glycemic control in adults with type 2 diabetes mellitus. Colesevelam hydrochloride is poly(allylamine hydrochloride) cross-linked with epichlorohydrin and alkylated with 1-bromodecane and (6-bromohexyl)-trimethylammonium bromide. The chemical name (IUPAC) of colesevelam hydrochloride is allylamine polymer with 1-chloro-2,3-epoxypropane, [6-(allylamino)-hexyl]trimethylammonium chloride and N-allyldecylamine, hydrochloride. The chemical structure of colesevelam hydrochloride is represented by the following formula:

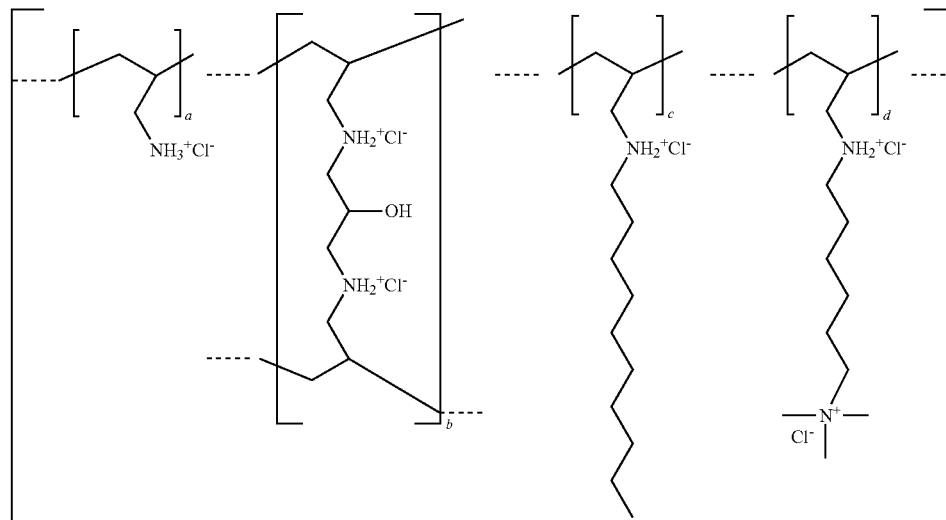

In exemplary embodiments, formulations of the disclosure may comprise active agent at a concentration of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80%, In exemplary embodiments, formulations of the disclosure may comprise active agent at a concentration of about 1 to 20%, of about 5% to 25%, about 10% to about 20%, or about 15% to about 18%, about 30% to about 70%, about 35% to about 65%, about 63.13%, and about 40% to about 64% w/w.

In exemplary tablets of the disclosure, the active agent will represent approximately 1 wt % to 75 wt %, preferably 2 wt % to 30 wt %, more preferably 5 wt. % to 20 wt. % of the core.

Gastrointestinal Tract

The small intestine extends from the pylorus to the colic valve where it ends in the large intestine. The small intestine is about 6 meters long and is divisible into three portions: the duodenum, the jejunum, and the ileum. The small intestine is especially adapted for transport and absorption of nutrients and other molecules from ingested material, passing through the lining of the small intestine into the blood. The surface cells of the small intestine are highly specialized for digestion and absorption of nutrients. Almost all the body's nutrient absorption occurs in the small intestine, along its three sub-divisions: the duodenum, jejunum, and ileum. Sites for absorption of specific nutrients (egg: iron, vitamin B12) are located in these divisions, but most absorption occurs in the jejunum (middle section). Specialized cells contain digestive enzymes, carrier proteins and other secretions. Blood vessels transport nutrients away from the intestine to the liver in the first instance.

Indigestible food passes into the large intestine. By the time ingested material leaves the small intestine, virtually all nutrient absorption will have occurred. The large intestine extends from the end of the ileum (distal ileum) to the anus. The large intestine is divided into the cecum, colon, rectum, and anal canal. The colon is divided into four parts: the ascending, transverse, descending, and sigmoid. The substantial release of the active agent of the present disclosure may occur in any portion of the large intestine. In one embodiment, release primarily occurs at the upper regions of the large intestine, such as, for example, at the distal ileum, cecum, and/or the ascending colon.

It is known that there are major variations in acidity in the gastrointestinal tract. The stomach is a region of high acidity (about pH 1 to 3). Specific glands and organs emptying into the small intestine raise the pH of the material leaving the stomach to approximately pH 6.0 to 6.5. The large intestine and the colon are about pH 6.4 to 7.0. The transit time through the small intestine is approximately three hours. In contrast, the transit time through the large intestine is approximately 35 hours.

Pruritic Conditions

According to the present disclosure, pruritus includes any itchy or pruritic condition, e.g., a sensation that causes the desire or reflex to scratch. In some embodiments, compositions and methods of the disclosure are used for the treatment of a subject suffering from a pruritic condition selected from the group consisting of atopic dermatitis, nervous dermatitis, contact dermatitis, seborrheic dermatitis, autosensitization dermatitis, caterpillar dermatitis, asteatosis, senile pruritus cutaneous, insect sting, photosensitive dermatosis, urticarial, prurigo, herpes, impetigo, eczema, tinea, lichen, psoriasis, scabies and acne vulgaris, visceral diseases complicated with pruritus such as malignant tumors, diabetes mellitus, hepatic diseases, renal failure, hemodialysis, peritoneal dialysis, and pregnancy. Chronic pruritus on non-inflamed skin may result from dermatological diseases, including atopic diathesis, asteatosis, porphyria, suburticarial stages of solar injury, cholinergic, adrenergic urticaria, initial stage of mastocytosis, bullous pemphigoid, and Duhring's disease (dermatitis herpetiformis); from endocrine and metabolic disorders, such as chronic renal insufficiency and the dialysis needed treat it, hepatopathies with cholestasis, diabetes mellitus, malabsorption disorders, anorexia, gluten-enteropathies, hyperthyroidism, hypothyroidism, hyperparathyroidism, and perimenopausal pruritus; from infections including HIV infection, parasites, Helicobacter pylori, and helminth-related; from hemotological and lymphoproliferative diseases such as iron deficiency, polycythaemica vera, hypereosinophilia syndrome, myelodysplastic syndrome, Hodgkin's disease, non-Hodgkin's lymphoma, plasmocytoma, and systemic mastocytosis; from solid malignant tumors including cervical, breast, prostate or large intestinal cancer, and carcinoid tumors; from neurological disorders such as brachioradial pruritus, notalgia paresthetica, post-zoster neuralgia, vulvodynia, neuropathies of various origin, multiple sclerosis, tumors, abscesses, underperfusion, infarctions involving the CNS/spinal cord; from psychogenic disorders such as depression, schizophrenia, and tactile hallucinations; and from intrahepatic cholestasis in pregnant women (pruritus gravidarum).

Chronic pruritus on inflamed skin may be observed in patients with inflammatory skin disease including, but not limited to, atopic dermatitis, allergic, irritant contact dermatitis, exsiccation dermatitis, nummular and dyshidrotic dermatitis, lichen planus, lichen sclerosus et atrophicus, polymorphous light eruption psoriasis, Grover's disease, mucinosis, mastocytosis, and urticaria; infectious skin diseases such as mycoses, bacterial and viral infections, scabies, pediculosis, insect bites, and folliculitides; autoimmune skin diseases including Bullous skin disorders, especially dermatitis herpetiformis (Duhring's disease), and bullous pemphigoid; genodermatoses such as Darier's disease, and Hailey-Hailey disease; pregnancy-related skin diseases including polymorphic eruption of pregnancy (PEP, formerly known as PUPPP), atopic eruption of pregnancy, and pemphigoid gestationis; and neoplasias such as cutaneous T-cell lymphoma (especially the erythrodermic form).

Prurigo nodularis (PN), or nodular prurigo, is a particularly severe form of chronic itching that may treated by methods and compositions of the present disclosure. Characterized by itchy, excoriated, lichenified papules and nodules, PN can occur at any age, but most often presents in middle-aged and elderly patients on their arms and legs (E. Weisshaar and S. Stander, Acta Derm. Venereol., 2012, 92:532-533). The etiology of PN is unknown, but it usually occurs in patients with a personal or family history of atopic dermatitis, and often with concomitant medical conditions such as hepatic or renal function, local trauma or insult to the skin, infection, and HIV or other immunodeficiencies. PN may result in permanent changes to the skin, including nodular lichenification, hyperkeratosis, hyperpigmentation, and skin thickening.

In some embodiments, methods of the present disclosure are used for the treatment of a subject suffering from a pruritic condition associated with a skin change. For example, such pruritic condition can be selected from the group consisting of pruritus secondary to inflamed skin (e.g., atopic dermatitis, psoriasis, burns); pruritus arising from conditions of non-diseased skin (e.g., uremic pruritus, cholestatic pruritus, cancers, hydroxyetheyl starch induced pruritus), and pruritus associated with chronic secondary scratch or other types of skin lesions that may or may not be the result of an underlying medical condition (e.g., prurigo nodularis) and the underlying disease is categorized based on histological, radiological or other investigations as being of an origin selected from the group consisting of dermatologic origin, systemic disease origin, neurologic origin, psychogenic origin, mixed origin, or other origin.

In some embodiments, compositions and methods of the present disclosure are used for the treatment of a subject suffering from a pruritic condition associated with neurogenic inflammation of the skin, e.g., prurigo nodularis, atopic dermatitis, burn pruritus, burn, wound healing, etc. In some other embodiments, methods of the present disclosure are used for the treatment of a subject suffering from a pruritic condition associated with neurogenic inflammation with elevated substance P level. In still some other embodiments, methods of the present disclosure are used for the treatment of a subject suffering from a pruritic condition associated with elevated substance P level.

In some embodiments, compositions and methods of the present disclosure are used for the treatment of a subject suffering from a pruritic condition associated with one or more related or unrelated conditions. For example, the pruritic condition can be associated with a dermatologic condition including aquagenic pruritus, atopic dermatitis, idiopathic pruritus, Lichen simplex chronicus, prurigo nodularis, psoriasis, and scabies. In another example, the pruritic condition can be associated with a hematological or oncological condition including cancer related pruritus, chemotherapy induced pruritus, HIV protease inhibitor induced pruritus, Hodgkin's lymphoma associated pruritus, polycythemia vera, etc. In another example, the pruritic condition can be associated with a metabolic condition including cholestatic pruritus, uremic pruritus, etc. In still another example, the pruritic condition can be associated with a condition of pain or neurological condition including brachioradial pruritus, burn induced pruritus, neuropathic pruritus, morphine induced pruritus, multiple sclerosis associated pruritus, post herpetic pruritus, pruritus associated with psychiatric causes, etc.

In one embodiment, compositions and methods of the present disclosure are used for the treatment of uremic pruritus. In another embodiment, methods of the present disclosure are used for the treatment of prurigo nodularis. In yet another embodiment, compositions and methods of the present disclosure are used to treat human beings. In still another embodiment, methods of the present disclosure are used to treat animals other than human beings.

Cardiovascular Disease

Aspects of the present specification disclose, in part, a method of treating an individual with a cardiovascular disease. In one embodiment, the method comprises the step of administering to an individual in need thereof a pharmaceutical composition disclosed herein, wherein administration reduces a symptom associated with the cardiovascular disease, thereby treating the individual.

Aspects of the present specification disclose, in part, treating an individual suffering from a cardiovascular disease. As used herein, the term "treating," refers to reducing or eliminating in an individual a clinical symptom of a cardiovascular disease; or delaying or preventing in an individual the onset of a clinical symptom of a cardiovascular disease. For example, the term "treating" can mean reducing a symptom of a condition characterized by a cardiovascular disease by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with a cardiovascular disease are well known and can be determined by a person of ordinary skill in the art by taking into account factors, including, without limitation, the location of the cardiovascular disease, the cause of the cardiovascular disease, the severity of the cardiovascular disease, and/or the tissue or organ affected by the cardiovascular disease. Those of skill in the art will know the appropriate symptoms or indicators associated with a specific type of cardiovascular disease and will know how to determine if an individual is a candidate for treatment as disclosed herein.

Cardiovascular disease is any of a number of specific diseases that affect the heart itself and/or the blood vessel system, especially the veins and arteries leading to and from the heart. Known and/or associated causes of a cardiovascular disease include, without limitation, unhealthy ratios of the two smallest lipoproteins LDL and HDL, hyperlipidemia, elevated blood glucose levels, upper normal and high blood pressure, Lp-PLA2, lipoprotein(a) and hyperhomocysteinemia. Symptoms of a cardiovascular disorder affecting the heart include, without limitation, chest pain, chest discomfort, and pain in one or both arms, one or both shoulders, neck, jaw, or back, shortness of breath, dizziness, faster heartbeats, nausea, abnormal heartbeats, fatigue, and/or myocardial infarction. Symptoms of a cardiovascular disorder affecting the brain include, without limitation, sudden numbness or weakness of the face, one or both arms, or one or both legs, sudden confusion or trouble speaking or understanding speech, sudden trouble seeing in one or both eyes, sudden dizziness, difficulty walking, or loss of balance or coordination, and/or sudden severe headache with no known cause. Symptoms of a cardiovascular disorder affecting one or both leg, pelvis, one or both arms, and/or shoulder include, without limitation, muscle pain, muscle cramp, cold sensation in one or both feet and/or toes, one or both hands and/or fingers, and/or numbness or weakness in one or both feet and/or toes, one or both hands and/or fingers.

There are more than 60 types of cardiovascular disease including, without limitation, a hyperlipidemia, a coronary heart disease, an atherosclerosis, a peripheral vascular disease, a cardiomyopathy, a vasculitis, an inflammatory heart disease, an ischemic heart disease, a congestive heart failure, a hypertensive heart disease, a valvular heart disease, a hypertension, myocardial infarction, a diabetic cardiac conditions, an aneurysm; an embolism, a dissection, a pseudoaneurysm, a vascular malformation, a vascular nevus, a thrombosis, a varicose vein, and a stroke.

In one embodiment, a cardiovascular disease comprises a hyperlipidemia. A hyperlipidemia (or hyperlipoproteinemia) refers to a condition characterized by abnormally elevated levels of lipids and/or lipoproteins in the blood. Hyperlipidemias may be classified as familial (or primary) when caused by specific genetic abnormalities, acquired (or secondary) when resulting from another underlying disorder, or idiopathic, when of unknown cause. Hyperlipidemias may also be classified based on which types of lipids and/or lipoproteins are elevated. Non-limiting examples of a hyperlipidemia include dyslipidemia, hypercholesterolemia, hyperglyceridemia, hypertriglyceridemia, hyperlipoproteinemia, and hyperchylomicronemia, and combined hyperlipidemia. Hyperlipoproteinemia include, e.g., hyperlipoproteinemia type Ia, hyperlipoproteinemia type Ib, hyperlipoproteinemia type Ic, hyperlipoproteinemia type IIa, hyperlipoproteinemia type IIb, hyperlipoproteinemia type III, hyperlipoproteinemia type IV, and hyperlipoproteinemia type V.

In another embodiment, a cardiovascular disease comprises a coronary heart disease. A coronary heart disease refers to a condition characterized by failure of the coronary circulation to supply adequate blood flow to cardiac muscle and surrounding tissue. Typically caused by the narrowing or blockage of the coronary artery, such as, e.g., an atherosclerotic coronary artery disease, a coronary vasospasm, and/or a coronary stenosis. Chest pain and myocardial infarction are common symptoms of and conditions caused by coronary heart disease.

In another embodiment, a cardiovascular disease comprises a vascular occlusive disease (VOD). A VOD refers to a condition characterized by an obstruction of a blood vessel. A VOD includes, without limitation, an atherosclerosis, a peripheral vascular disease, and a stenosis. In an aspect of this embodiment, a VOD comprises an atherosclerosis. An atherosclerosis refers to a condition characterized by a buildup of cholesterol and fatty deposits (called plaques) on the inner walls of the arteries. These plaques can restrict blood flow to the heart muscle by physically clogging the artery or by causing abnormal artery tone and function. Rupture of atherosclerotic plaque is the most common cause of an ischemia.

In an aspect of this embodiment, a VOD comprises a peripheral vascular disease (PVD). Peripheral vascular disease (PVD), also known as peripheral arterial disease (PAD) or peripheral artery occlusive disease (PAOD), refers to a condition characterized by an obstruction of large arteries not within the coronary, aortic arch vasculature, or brain. PVD can result from atherosclerosis, an inflammatory processes leading to stenosis, an embolism, or thrombus formation. It causes either acute or chronic ischemia. PVD also includes a subset of diseases classified as microvascular diseases resulting from episodic narrowing of the arteries, such as, e.g., Raynaud's phenomenon, or widening of the arteries, such as, e.g., a vascular spasm. Symptoms of PVD include, without limitation, pain, weakness, numbness, or cramping in muscles due to decreased blood flow, sores, wounds, or ulcers that heal slowly or not at all, blueness or paleness in limb, coolness in limb, diminished hair and nail growth on affected limb and digits. About 20% of patients with mild PAD may be asymptomatic.

In another embodiment, a cardiovascular disease comprises a cardiomyopathy. A cardiomyopathy refers to a condition characterized by the deterioration of myocardium function. Symptoms and signs may mimic those of almost any form of heart disease and include chest pain and EKG abnormalities. A mild cardiomyopathy is frequently asymptomatic. A more severe case is associated with heart failure, arrhythmias, systemic embolization and/or sudden cardiac death. A cardiomyopathy may be classified functionally, as involving dilation, hypertrophy, or restriction.

In another embodiment, a cardiovascular disease comprises a vasculitis. Vasculitis is a varied group of disorders featuring inflammation of a vessel wall including lymphatic vessels and blood vessels like veins (phlebitis), arteries (arteritis) and capillaries due to leukocyte migration and resultant damage. In another embodiment, a cardiovascular disease comprises an inflammatory heart disease. An inflammatory heart disease refers to a condition characterized by inflammation of the heart muscle and/or the tissue surrounding it. Non-limiting examples of inflammatory heart disease include endocarditis, inflammatory cardiomegaly, and myocarditis.

In another embodiment, a cardiovascular disease comprises an ischemic heart disease. Ischemic heart disease, or myocardial ischemia, refers to a condition characterized by reduced blood supply of the heart muscle, usually due to a narrowing or blockage of a coronary artery. Symptoms of ischemic heart disease include chest pain on exertion, in cold weather or emotional situations, acute chest pain, acute coronary syndrome, unstable angina, myocardial infarction, heart failure, difficulty in breathing or swelling of the extremities.

In another embodiment, a cardiovascular disease comprises a congestive heart failure. A congestive heart failure, or congestive cardiac failure, refers to a condition characterized by a heart abnormality that cannot result from any structural or functional cardiac disorder that impairs the ability of the heart to fill with or pump a sufficient amount of blood throughout the body.

In another embodiment, a cardiovascular disease comprises a hypertensive heart disease. A hypertensive heart disease refers to a condition characterized by high blood pressure, especially localized high blood pressure. Conditions that can be caused by hypertensive heart disease include, without limitation, left ventricular hypertrophy, coronary heart disease, congestive heart failure, hypertensive cardiomyopathy, and cardiac arrhythmias.

In another embodiment, a cardiovascular disease comprises a valvular heart disease. A valvular heart disease refers to a condition characterized by a malfunction of one or more valves of the heart. Major heart valves which may be affected by valvular heart disease, including, without limitation, tricuspid valve, right aortic valve, mitral valve, and left aortic valve.

A composition or compound is administered to an individual. An individual is typically a human being. Typically, any individual who is a candidate for a conventional cardiovascular disease treatment is a candidate for a cardiovascular disease treatment disclosed herein. Pre-operative evaluation typically includes routine history and physical examination in addition to thorough informed consent disclosing all relevant risks and benefits of the procedure.

The compounds and compositions as disclosed, for example, bile acid sequestrants such as cholestyramine, colestipol, and colesevelam, may also be advantageously combined and/or used in combination with other lipid-regulating agents, different from the subject compounds. In many instances, administration in combination with the disclosed compounds and compositions enhances the efficacy of such modulators. Lipid-regulating agents may include, but are not limited to, statins, otherwise known as HMG-CoA reductase inhibitors, such as mevastatin, pravastatin, atorvastatin, rosuvastatin, cerivastatin, fluvastatin, lovastatin, and simvastatin; niacin, or nicotinic acid, and its derivatives; fibrates such as gemfibrozil, clofibrate, fenofibrate, benzafibrate and cipofibrate; probucol; raloxifene and its derivatives; absorption inhibitors such as ACAT inhibitors, β-lactam, sulfated polysaccharides, steroidal glycosides, and azetidinone compounds, including but not limited to ezetimibe, and others described above; unsaturated omega-3 fatty acids; and mixtures thereof.

Diabetes and Related Disorders

The drugs or combinations as disclosed herein may be used to normalize blood glucose level by acting e.g., on insulin release, glucagon release, glucose utilization and/or glucose production, and offer novel potent therapies of diabetes and related disorders. The drugs and combinations have a strong effect on diabetes' relevant functions: they are involved in the protection of beta cells against apoptosis, the increase of glucose uptake in muscular tissues and in adipocytes, the increase of insulin secretion by the pancreatic β cells and/or in the control of glucose production in hepatic tissues.

These drugs and combinations therefore represent new therapeutic approaches for the control of blood glucose level in a mammalian in need thereof. They also represent new therapeutic approaches for the treatment of diabetes or related disorders in a mammalian in need thereof.

In this regard, aspects of the present specification relate to compositions comprising at least one compound selected from the group consisting of colesevelam, pharmaceutically acceptable salts thereof, derivatives thereof, and combinations thereof to a patient in need thereof. Aspects of the present specification relate to compositions comprising bile acid sequestrants such as cholestyramine, colestipol, and colesevelam.

Aspects of the present specification also relates to the use of at least one compound selected from the group consisting of colesevelam, pharmaceutically acceptable salts thereof, derivatives thereof, and combinations thereof for the manufacture of a medicament for treating diabetes or a related disorder in a patient in need thereof. Aspects of the present specification also relates to the use of bile acid sequestrants such as cholestyramine, colestipol, and colesevelam for the manufacture of a medicament for treating diabetes or a related disorder in a patient in need thereof Within the scope of the present disclosure it has now surprisingly been found that at least one compound selected from the group consisting of colesevelam, pharmaceutically acceptable salts thereof, derivatives thereof, and combinations thereof as defined herein have unexpected and particularly advantageous properties, which make them particularly suitable for treating and/or preventing (including preventing or slowing the progression or delaying the onset) of metabolic diseases, particularly diabetes (especially type 2 diabetes mellitus) and conditions related thereto (e.g., diabetic complications), in advanced or late stage type 2 diabetes patients, including patients with insufficient glycemic control despite a therapy with an oral and/or a non-oral antidiabetic drug and/or with indication on insulin.

Thus, the present disclosure provides at least one compound selected from the group consisting of colesevelam, pharmaceutically acceptable salts thereof, derivatives thereof, and combinations thereof as defined herein for use in the treatment of patients with insufficient glycemic control despite a therapy (including mono-, dual or triple medication) with one or more conventional oral antidiabetic drugs selected from metformin, sulphonylureas, thiazolidinediones, glinides and α-glucosidase inhibitors.

In another embodiment, the present disclosure provides at least one compound selected from the group consisting of colesevelam, pharmaceutically acceptable salts thereof, derivatives thereof, and combinations thereof as defined herein for use in the treatment of patients with insufficient glycemic control despite therapy (including mono-, dual or triple medication) with one, two or three conventional oral or non-oral antidiabetic drugs selected from metformin, sulphonylureas, thiazolidinediones, glinides, alpha-glucosidase blockers, GLP-1 and GLP-1 analogues, and insulin and insulin analogues; for example, despite mono-therapy with metformin, a sulphonylurea, pioglitazone or (basal) insulin, or despite dual combination therapy with a metformin/pioglitazone, metformin/sulphonylurea, metformin/(basal) insulin, sulphonylurea/pioglitazone, sulphonylurea/(basal) insulin or pioglitazone/(basal) insulin combination.

The present disclosure further provides at least one compound selected from the group consisting of colesevelam, pharmaceutically acceptable salts thereof, derivatives thereof, and combinations thereof as defined herein for use in the treatment of diabetes patients with insufficient glycemic control despite mono-therapy with a sulphonylurea, or despite dual combination therapy with a metformin/sulphonylurea, sulphonylurea/pioglitazone or sulphonylurea/(basal) insulin combination.

In particular, the present disclosure provides at least one compound selected from the group consisting of colesevelam, pharmaceutically acceptable salts thereof, derivatives thereof, and combinations thereof as defined herein for use in the treatment of patients with insufficient glycemic control despite a therapy with a sulphonylurea drug.

The present disclosure further provides at least one compound selected from the group consisting of colesevelam, pharmaceutically acceptable salts thereof, derivatives thereof, and combinations thereof as defined herein for use in the treatment and/or prevention of metabolic diseases, particularly type 2 diabetes mellitus, in patients with insufficient glycemic control despite a therapy with a sulphonylurea drug.

The present disclosure further provides at least one compound selected from the group consisting of colesevelam, pharmaceutically acceptable salts thereof, derivatives thereof, and combinations thereof as defined herein for use in the treatment and/or prevention of diabetes with secondary sulphonylurea failure.

The present disclosure further provides the use of at least one compound selected from the group consisting of colesevelam, pharmaceutically acceptable salts thereof, derivatives thereof, and combinations thereof as defined herein for the manufacture of a pharmaceutical composition for treating and/or preventing metabolic diseases, particularly type 2 diabetes mellitus, in patients with insufficient glycemic control despite a therapy with a sulphonylurea drug.

The present disclosure further provides a pharmaceutical composition for use in the treatment and/or prevention of metabolic diseases, particularly type 2 diabetes mellitus, in patients with insufficient glycemic control despite a therapy with a sulphonylurea drug, said pharmaceutical composition comprising at least one compound selected from the group consisting of colesevelam, pharmaceutically acceptable salts thereof, derivatives thereof, and combinations thereof as defined herein and optionally one or more pharmaceutically acceptable carriers and/or diluents.

Aspects of the specification relate to a fixed or non-fixed combination including a kit-of-parts for use in the treatment and/or prevention of metabolic diseases, particularly type 2 diabetes mellitus, in patients with insufficient glycemic control despite a therapy with a sulphonylurea drug, said combination comprising a At least one compound selected from the group consisting of colesevelam, pharmaceutically acceptable salts thereof, derivatives thereof, and combinations thereof as defined herein and optionally one or more other active substances, e.g., any of those mentioned herein.

The present disclosure further provides the use of at least one compound selected from the group consisting of colesevelam, pharmaceutically acceptable salts thereof, derivatives thereof, and combinations thereof as defined herein in combination with one or more other active substances, such as e.g., any of those mentioned herein, for the manufacture of a pharmaceutical composition for treatment and/or prevention of metabolic diseases, particularly type 2 diabetes mellitus, in patients with insufficient glycemic control despite a therapy with a sulphonylurea drug.

The present disclosure further provides a pharmaceutical composition for use in the treatment and/or prevention of metabolic diseases, particularly type 2 diabetes mellitus, in patients with insufficient glycemic control despite a therapy with a sulphonylurea drug, said pharmaceutical composition comprising at least one compound selected from the group consisting of colesevelam, pharmaceutically acceptable salts thereof, derivatives thereof, and combinations thereof as defined herein and optionally one or more other active substances, such as e.g., any of those mentioned herein, such as e.g., for separate, sequential, simultaneous, concurrent or chronologically staggered use of the active ingredients.

The present disclosure further provides a method of treating and/or preventing metabolic diseases, particularly type 2 diabetes mellitus, in patients with insufficient glycemic control despite a therapy with a sulphonylurea drug, said method comprising administering to a subject in need thereof (particularly a human patient) an effective amount of at least one compound selected from the group consisting of colesevelam, pharmaceutically acceptable salts thereof, derivatives thereof, and combinations thereof as defined herein, optionally alone or in combination, such as e.g., separately, sequentially, simultaneously, concurrently or chronologically staggered, with an effective amount of one or more other active substances, such as e.g., any of those mentioned herein.

In addition, aspects of the specification relate to at least one compound selected from the group consisting of colesevelam, pharmaceutically acceptable salts thereof, derivatives thereof, and combinations thereof as defined herein, optionally in (add-on or initial) combination with one or two conventional antihyperglycemic agents selected from metformin, sulphonylureas, thiazolidinediones (e.g., pioglitazone), glinides, alpha-glucosidase blockers, GLP-1 or GLP-1 analogues, and insulin or insulin analogues, for use in patients with insufficient glycemic control despite therapy with (e.g., if applicable, despite therapy with a maximal tolerated oral dose of) one, two or three conventional antihyperglycemic agents selected from metformin, sulphonylureas, thiazolidinediones, glinides, alpha-glucosidase blockers, GLP-1 or GLP-1 analogues, and insulin or insulin analogues (e.g., despite mono-therapy with metformin, a sulphonylurea, pioglitazone or (basal) insulin, or despite dual combination therapy with a metformin/pioglitazone, metformin/sulphonylurea, metformin/(basal) insulin, sulphonylurea/pioglitazone, sulphonylurea/(basal) insulin or pioglitazone/(basal) insulin combination).

In a further embodiment of the present disclosure, it is provided at least one compound selected from the group consisting of colesevelam, pharmaceutically acceptable salts thereof, derivatives thereof, and combinations thereof as defined herein, optionally in combination with one conventional antihyperglycemic agent selected from metformin, sulphonylureas, thiazolidinediones (e.g., pioglitazone), glinides, alpha-glucosidase blockers, GLP-1 and GLP-1 analogues, and insulin and insulin analogues, for use in (second line) therapy of type 2 diabetes patients who are insufficiently controlled on said conventional antihyperglycemic agent alone.

In a further embodiment of the present disclosure, it is provided at least one compound selected from the group consisting of colesevelam, pharmaceutically acceptable salts thereof, derivatives thereof, and combinations thereof as defined herein, optionally in combination with two conventional antihyperglycemic agents selected from metformin, sulphonylureas, thiazolidinediones (e.g., pioglitazone), glinides, alpha-glucosidase blockers, GLP-1 and GLP-1 analogues, and insulin and insulin analogues, for use in (third line) therapy of type 2 diabetes patients who are insufficiently controlled on a dual combination of said conventional antihyperglycemic agents.

In a further embodiment of the present disclosure, it is provided at least one compound selected from the group consisting of colesevelam, pharmaceutically acceptable salts thereof, derivatives thereof, and combinations thereof as defined herein, in combination with a conventional antihyperglycemic agent selected from the group consisting of metformin, pioglitazone, a sulphonylurea, and insulin; for use in therapy of type 2 diabetes patients with insufficient glycemic control on the conventional antihyperglycemic agent alone.

In a further embodiment of the present disclosure, it is provided at least one compound selected from the group consisting of colesevelam, pharmaceutically acceptable salts thereof, derivatives thereof, and combinations thereof as defined herein, in combination with two conventional antihyperglycemic agents selected from the group consisting of the following combinations: metformin and pioglitazone, metformin and a sulphonylurea, metformin and insulin, a sulphonylurea and pioglitazone, a sulphonylurea and insulin, and pioglitazone and insulin; for use in therapy of type 2 diabetes patients with insufficient glycemic control on the two conventional antihyperglycemic agents.

In particular, the present disclosure provides at least one compound selected from the group consisting of colesevelam, pharmaceutically acceptable salts thereof, derivatives thereof, and combinations thereof as defined herein in combination with a sulphonylurea for use in the treatment of type 2 diabetes patients with insufficient glycemic control despite mono-therapy with a maximal tolerated dose of a sulphonylurea.

Further, the present disclosure provides at least one compound selected from the group consisting of colesevelam, pharmaceutically acceptable salts thereof, derivatives thereof, and combinations thereof as defined herein in combination with a sulphonylurea and metformin for use in the treatment of type 2 diabetes patients with insufficient glycemic control despite dual combination therapy with a sulphonylurea and metformin.

Further, the present disclosure provides at least one compound selected from the group consisting of colesevelam, pharmaceutically acceptable salts thereof, derivatives thereof, and combinations thereof as defined herein in combination with a sulphonylurea and pioglitazone for use in the treatment of type 2 diabetes patients with insufficient glycemic control despite dual combination therapy with a sulphonylurea and pioglitazone.

Further, the present disclosure provides at least one compound selected from the group consisting of colesevelam, pharmaceutically acceptable salts thereof, derivatives thereof, and combinations thereof as defined herein in combination with a sulphonylurea and insulin for use in the treatment of type 2 diabetes patients with insufficient glycemic control despite dual combination therapy with a sulphonylurea and insulin.

The present disclosure further provides the use of at least one compound selected from the group consisting of colesevelam, pharmaceutically acceptable salts thereof, derivatives thereof, and combinations thereof as defined herein, optionally in combination with one or more other active substances, such as e.g., any of those mentioned herein, for one or more of the following purposes:

for preventing, slowing progression of, delaying, or treating a metabolic disorder;

for improving glycemic control and/or for reducing of fasting plasma glucose, of postprandial plasma glucose and/or of glycosylated hemoglobin HbA1c;

for preventing, slowing progression of, delaying or treating of a condition or disorder selected from the group consisting of complications of diabetes mellitus;

for reducing the weight or preventing an increase of the weight or facilitating a reduction of the weight;

for preventing or treating the degeneration of pancreatic beta cells and/or for improving and/or restoring the functionality of pancreatic beta cells and/or stimulating and/or restoring the functionality of pancreatic insulin secretion; and/or for maintaining and/or improving the insulin sensitivity and/or for treating or preventing hyperinsulinemia and/or insulin resistance; in diabetes patients with insufficient glycemic control despite a therapy with an oral antidiabetic drug, particularly a sulphonylurea drug (secondary SU failure).

Examples of such metabolic diseases or disorders amenable by the therapy of this disclosure in patients with secondary oral antidiabetic drug failure may include, without being restricted to, Type 1 diabetes, Type 2 diabetes, inadequate glucose tolerance, insulin resistance, hyperglycemia, hyperlipidemia, hypercholesterolemia, dyslipidemia, metabolic syndrome X, obesity, hypertension, chronic systemic inflammation, retinopathy, neuropathy, nephropathy, atherosclerosis, endothelial dysfunction and osteoporosis.

The present disclosure further provides the use of at least one compound selected from the group consisting of colesevelam, pharmaceutically acceptable salts thereof, derivatives thereof, and combinations thereof as defined herein, optionally in combination with one or more other active substances, such as e.g., any of those mentioned herein, for the manufacture of a medicament for one or more of the following purposes:

preventing, slowing the progression of, delaying or treating a metabolic disorder or disease, such as e.g., type 1 diabetes mellitus, type 2 diabetes mellitus, impaired glucose tolerance (IGT), impaired fasting blood glucose (IFG), hyperglycemia, postprandial hyperglycemia, overweight, obesity, dyslipidemia, hyperlipidemia, hypercholesterolemia, hypertension, atherosclerosis, endothelial dysfunction, osteoporosis, chronic systemic inflammation, non alcoholic fatty liver disease (NAFLD), retinopathy, neuropathy, nephropathy and/or metabolic syndrome;

improving glycemic control and/or for reducing of fasting plasma glucose, of postprandial plasma glucose and/or of glycosylated hemoglobin HbA1c;

preventing, slowing, delaying or reversing progression from impaired glucose tolerance (IGT), impaired fasting blood glucose (IFG), insulin resistance and/or from metabolic syndrome to type 2 diabetes mellitus;

preventing, reducing the risk of, slowing the progression of, delaying or treating of complications of diabetes mellitus such as micro- and macrovascular diseases, such as nephropathy, micro- or macroalbuminuria, proteinuria, retinopathy, cataracts, neuropathy, learning or memory impairment, neurodegenerative or cognitive disorders, cardio- or cerebrovascular diseases, tissue ischaemia, diabetic foot or ulcus, atherosclerosis, hypertension, endothelial dysfunction, myocardial infarction, acute coronary syndrome, unstable angina pectoris, stable angina pectoris, peripheral arterial occlusive disease, cardiomyopathy, heart failure, heart rhythm disorders, vascular restenosis, and/or stroke;

reducing body weight or preventing an increase in body weight or facilitating a reduction in body weight;

preventing, slowing, delaying or treating the degeneration of pancreatic beta cells and/or the decline of the functionality of pancreatic beta cells and/or for improving and/or restoring the functionality of pancreatic beta cells and/or stimulating and/or restoring the functionality of pancreatic insulin secretion;

preventing, slowing, delaying or treating non alcoholic fatty liver disease (NAFLD) including hepatic steatosis, non-alcoholic steatohepatitis (NASH) and/or liver fibrosis;

preventing, slowing the progression of, delaying or treating type 2 diabetes with primary or secondary failure to conventional (oral) antihyperglycemic mono- or combination therapy;

achieving a reduction in the dose of conventional antihyperglycemic medication required for adequate therapeutic effect;

reducing the risk for adverse effects associated with conventional antihyperglycemic medication; and/or maintaining and/or improving the insulin sensitivity and/or for treating or preventing hyperinsulinemia and/or insulin resistance;

particularly in a patient with insufficient glycemic control despite mono- or dual or triple combination therapy with conventional oral or non-oral antidiabetic drug(s) selected from metformin, sulphonylureas, thiazolidinediones (e.g., pioglitazone), glinides, alpha-glucosidase blockers, GLP-1 and GLP-1 analogues, and insulin and insulin analogues.

Pharmaceutical Compositions

Methods by which to formulate compositions to target specific regions of the gastrointestinal tract, such as the colon, include, for example, release of drug in the gastrointestinal tract may be accomplished by choosing a drug release controlling component to work together with some physical, chemical or biochemical process in the gastrointestinal tract. A drug release controlling component may take advantage of processes and/or conditions within the gastrointestinal tract and in specific regions of the gastrointestinal tract such as, for example, osmotic pressure, hydrodynamic pressure, vapor pressure, mechanical action, hydration status, pH, bacterial flora, and enzymes.

Optionally, pharmaceutical compositions of the present disclosure including drug cores may further comprise a seal coating material that seals the drug to prevent decomposition due to exposure to moisture, such as hydroxypropylmethylcellulose. Accordingly, the drug core of the pharmaceutical composition (containing the active agent) may first be sealed with the seal coating material and then coated with the drug release controlling component to prevent decomposition of the active agent by exposure to moisture. Seal coating materials include, in one embodiment, acetyltributyl citrate, acetyltriethyl citrate, calcium carbonate, carauba wax, cellulose acetate, cellulose acetate phthalate, cetyl alcohol, chitosan, ethylcellulose, fructose, gelatin, glycerin, glyceryl behenate, glyceryl palmitostearate, hydroxyethyl cellulose, hydroxyethylmethyl cellulose, hydroxypropyl cellulose, hypromellose, hypromellose phthalate, isomalt, latex particles, maltitol, maltodextrin, methylcellulose, microcrystalline wax, paraffin, poloxamer, polydextrose, polyethylene glycol, polyvinyl acetate phthalate, polyvinyl alcohol, povidone, shellac, shellac with stearic acid, sodium carboxymethyl cellulose, sucrose, titanium oxide, tributyl citrate, triethyl citrate, vanillin, white wax, xylitol, yellow wax, and zein. Compositions of the present disclosure may also include film forming agents, which include, for example, ammonium alginate, calcium carbonate, chitosan, chlorpheniramine maleate, copovidone, dibutyl phthalate, dibutyl sebacate, diethyl phthalate, dimethyl phthalate, ethyl lactate, ethylcellulose, gelatin, hydroxyyethyl cellulose, hydroxypropyl cellulose, hypromellose, hypromellose acetate succinate, maltodextrin, polydextrose, polyethylene glycol, polyethylene oxide, polymethylacrylates, poly(methylvinyl ether/maleic anhydride), polyvinylacetate phthalate, triethyl citrate, and vanillin. The amount of seal coating will vary in accordance with factors known by those of skill in the art. The amount of seal coat is, in one embodiment about 0.1% of the drug core, about 0.2% of the drug core, about 0.3% of the drug core, about 0.4% of the drug core, about 0.5% of the drug core, about 0.6% of the drug core, about 0.7% of the drug core, about 0.8% of the drug core, about 0.9% of the drug core, about 1% w/w of the drug core; about 2%, w/w of the drug core, about 3%, w/w, of the drug core, about 4%, w/w, of the drug core; about 5% w/w of the drug core; about 6%, w/w of the drug core, about 7%, w/w, of the drug core, about 8%, w/w, of the drug core; about 9% w/w of the drug core; about 10%, w/w of the drug core, about 11%, w/w, of the drug core, about 12%, w/w, of the drug core; about 14% w/w of the drug core; about 16%, w/w of the drug core, about 18%, w/w, of the drug core, about 20%, w/w, of the drug core; or more, if determined to be appropriate. Seal coats may also be applied at amounts between about 1% and about 10% w/w of the drug core, between about 2% and 9% w/w of the drug core, between about 3% and 8% w/w of the drug core, between about 4% and 7% w/w of the drug core, and between about 5% and about 6% w/w of the drug core.

In one embodiment, drug release controlling components include, for example, coatings, matrices, or physical changes. Coatings are used in one embodiment. Coatings include, for example, enteric coatings, time delay coatings, bacterially degradable coatings, and mixtures thereof. The pharmaceutical composition may comprise multiple coatings of either the same or different types of coatings. In choosing an appropriate coating or mixture thereof, the formulations practitioner may consider a number of variables influencing the location in which a drug will become available in the gastrointestinal tract, e.g., the pH at which coatings dissolve; the time of dissolution (which is influenced by thickness of the coatings and/or additional components in the coatings); time of transit through the gastrointestinal tract, and whether the coatings can be degraded by the patent's digestive enzymes or require enzymes present only in bacteria residing in the lower intestine. As an example of a combination drug release controlling component is, for example, an inner core with two polymeric layers. The outer layer, an enteric coating, may be chosen to dissolve at a pH level above 5. The inner layer, may be made up of hydroxypropylmethylcellulose to act as a time delay component to delay drug release for a predetermined period. The thickness of the inner layer can be adjusted to determine the lag time.

Methods by which skilled practitioners can assess where a drug is released in the gastrointestinal tract of patients are known in the art, and include scintigraphic studies, testing in biorelevant medium which simulates the fluid in relevant portions of the gastrointestinal tract, among others.

In certain embodiments, the active agent is released in, for example, the large intestine. In certain embodiments, the active agent is released in the large intestine in an amount selected from the group consisting of about 70%, about 75%, about 80%, about 85%, about 90%, about 95%, and about 100% w/w of the active agent present in the formulation. In certain embodiments, the active agent is released in the large intestine in an amount of about 80% to about 100% w/w of the active agent present in the formulation.

In one embodiment, a drug release controlling component may include an enteric coating. The term "enteric coating" refers to a coating that allows an active agent formulation to pass through the stomach substantially intact and subsequently disintegrate substantially in the intestines. In one embodiment, the disintegration occurs in the large intestine.

In one embodiment, at least one active agent is incorporated into an erodible or non-erodible polymeric matrix controlled release device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or "matrix" that entraps the solubility-improved form of the active agent. The aqueous-swollen matrix gradually erodes, swells, disintegrates or dissolves in the environment of use, thereby controlling the release of the active agent to the environment of use. The erodible polymeric matrix into which the active agent is incorporated may generally be described as a set of excipients that are mixed with the solubility-improved form following its formation that, when contacted with the aqueous environment of use imbibes water and forms a water-swollen gel or "matrix" that entraps the drug form. Drug release may occur by a variety of mechanisms: the matrix may disintegrate or dissolve from around particles or granules of the drug in solubility-improved form; or the drug may dissolve in the imbibed aqueous solution and diffuse from the tablet, beads or granules of the device. A key ingredient of this water-swollen matrix is the water-swellable, erodible, or soluble polymer, which may generally be described as an osmopolymer, hydrogel or water-swellable polymer. Such polymers may be linear, branched, or crosslinked. They may be homopolymers or copolymers. Although they may be synthetic polymers derived from vinyl, acrylate, methacrylate, urethane, ester and oxide monomers, they are most preferably derivatives of naturally occurring polymers such as polysaccharides or proteins.

The term "cellulosic polymer" is used herein to denote a linear polymer of anhydroglucose. Cellulosic polymers that can be used advantageously in the present dosage forms include, without limitation, hydroxymethylcellulose, hydroxypropylcellulose, hydroxyethylcellulose, hydroxypropyl methylcellulose, methylcellulose, ethylcellulose, cellulose acetate, cellulose acetate phthalate, cellulose acetate trimellitate, hydroxypropyl methylcellulose phthalate, hydroxypropylcellulose phthalate, cellulose hexahydrophthalate, cellulose acetate hexahydrophthalate, carboxymethylcellulose, carboxymethylcellulose sodium, and microcrystalline cellulose. Preferred cellulosic polymers are alkyl-substituted cellulosic polymers that ultimately dissolve in the GI tract in a predictably delayed manner. Preferred alkyl-substituted cellulose derivatives are those substituted with alkyl groups of 1 to 3 carbon atoms each. Examples are methylcellulose, hydroxymethylcellulose, hydroxyethylcellulose, hydroxypropylcellulose, hydroxypropyl methylcellulose, and carboxymethylcellulose. In terms of their viscosities, one class of preferred alkyl-substituted celluloses includes those whose viscosity is within the range of about 50 to about 110,000 centipoise as a 2% aqueous solution at 20° C. Another class includes those whose viscosity is within the range of about 800 to about 6,000 centipoise as a 1% aqueous solution at 20° C. Particularly preferred alkyl-substituted celluloses are hydroxyethylcellulose and hydroxypropylmethylcellulose. A presently preferred hydroxyethylcellulose is NATRASOL® 250HX NF (National Formulary), available from Aqualon Company, Wilmington, Del., USA.

Polyalkylene oxides are the preferred polymers herein, and the polyalkylene oxides that are of greatest utility are those having the properties described above for alkyl-substituted cellulose polymers. A particularly preferred polyalkylene oxide is poly(ethylene oxide), which term is used herein to denote a linear polymer of unsubstituted ethylene oxide. Poly(ethylene oxide)s are often characterized by their viscosity in solution. For purposes of this disclosure, a preferred viscosity range is about 50 to about 2,000,000 centipoise for a 2% aqueous solution at 20° C. Preferred poly(ethylene oxide)s are those available in the Polyox® family of trademarks, e.g., Polyox 303, Polyox Coag, Polyox 301, Polyox WSR N-60K, Polyox WSR 1105 and Polyox WSR N-80, having number average molecular weights of 7 million, 5 million, 4 million, 2 million, 900,000 and 200,000, respectively, all products of Union Carbide Chemicals and Plastics Company Inc. of Danbury, Conn., USA.

Polysaccharide gums, both natural and modified (semi-synthetic) can be used. Examples are dextran, xanthan gum, gellan gum, welan gum and rhamsan gum. Xanthan gum is preferred.

Crosslinked polyacrylic acids of greatest utility are those whose properties are the same as those described above for alkyl-substituted cellulose and polyalkylene oxide polymers. Preferred crosslinked polyacrylic acids are those with a viscosity ranging from about 4,000 to about 40,000 centipoise for a 1% aqueous solution at 25° C. Three presently preferred examples are CARBOPOL® NF grades 971 P, 974P and 934P (BF Goodrich Co., Specialty Polymers and Chemicals Div., Cleveland, Ohio, USA). Further examples are polymers known as WATER LOCK®, which are starch/acrylates/acrylamide copolymers available from Grain Processing Corporation, Muscatine, Iowa, USA.

Suitable polymers also include naturally occurring hydrophilic polymers such as, by way of example, proteins such as collagen, fibronectin, albumins, globulins, fibrinogen, fibrin and thrombin; aminated polysaccharides, particularly the glycosaminoglycans, e.g., hyaluronic acid, chitin, chondroitin sulfate A, B, or C, keratin sulfate, keratosulfate and heparin; guar gum; xanthan gum; carageenan; alginates; pectin; and activated polysaccharides such as dextran and starches.

The aforementioned list of polymers is not exhaustive, and a variety of other synthetic hydrophilic polymers may be used, as will be appreciated by those skilled in the art.

The polymer may include biodegradable segments and blocks, distributed either throughout the polymer's molecular structure or present as a single block, as in a block copolymer. Biodegradable segments are those that degrade so as to break covalent bonds. Typically, biodegradable segments are segments that are hydrolyzed in the presence of water. Biodegradable segments may be composed of small molecular segments such as ester linkages, anhydride linkages, ortho ester linkages, ortho carbonate linkages, amide linkages, phosphonate linkages, etc.

Any polymer or polymers of the matrix may also be crosslinked, with the degree of crosslinking directly affecting the rate of polymer swelling as well as the erosion rate. That is, a polymer having a higher degree of crosslinking will exhibit less swelling and slower erosion than a polymer having a lower degree of crosslinking. Crosslinked polymers may be prepared using the above-mentioned exemplary polymers using conventional crosslinking procedures (e.g., chemical crosslinking with an added crosslinking agent, photolytically induced crosslinking, etc.), or the polymers may be obtained commercially in crosslinked form.

The water-swellable polymers can be used individually or in combination. Certain combinations will often provide a more controlled release of the drug than their components when used individually. Examples include, but are not limited to, the following: a cellulosic polymer combined with a gum, such as hydroxyethylcellulose or hydroxypropylcellulose combined with xanthan gum; a polyalkylene oxide combined with a gum, such as poly(ethylene oxide) combined with xanthan gum; and a polyalkylene oxide combined with a cellulosic polymer, such as poly(ethylene oxide) combined with hydroxyethylcellulose or hydroxypropylcellulose.

Combinations of different poly(ethylene oxide)s are also contemplated, with polymers of different molecular weights contributing to different dosage form characteristics. For example, a very high molecular weight poly(ethylene oxide) such as Polyox 303 (with a number average molecular weight of 7 million) or Polyox Coag (with a number average molecular weight of 5 million) may be used to significantly enhance diffusion relative to disintegration release by providing high swelling as well as tablet integrity. Incorporating a lower molecular weight poly(ethylene oxide) such as Polyox WSR N-60K (number average molecular weight approximately 2 million) with Polyox 303 and/or Polyox Coag increases disintegration rate relative to diffusion rate, as the lower molecular weight polymer reduces swelling and acts as an effective tablet disintegrant. Incorporating an even lower molecular weight poly(ethylene oxide) such as Polyox WSR N-80 (number average molecular weight approximately 200,000) further increases disintegration rate.

The hydrophilicity and water swellability of these polymers cause the drug-containing matrices to swell in size in the gastric cavity due to ingress of water in order to achieve a size that will be retained in the stomach when introduced during the fed mode. These qualities also cause the matrices to become slippery, which provides resistance to peristalsis and further promotes their retention in the stomach. The release rate of a drug from the matrix is primarily dependent upon the rate of water imbibition and the rate at which the drug dissolves and diffuses from the swollen polymer, which in turn is related to the solubility and dissolution rate of the drug, the drug particle size and the drug concentration in the matrix.

The amount of polymer relative to the drug can vary, depending on the drug release rate desired and on the polymer, its molecular weight, and excipients that may be present in the formulation. The amount of polymer will be sufficient however to retain at least about 40% of the drug within the matrix one hour after ingestion (or immersion in the gastric fluid). Preferably, the amount of polymer is such that at least 50% of the drug remains in the matrix one hour after ingestion. More preferably, at least 60%, and most preferably at least 80%, of the drug remains in the matrix one hour after ingestion. In all cases, however, substantially all of the drug will be released from the matrix within about eight hours, and preferably within about six hours, after ingestion, "substantially all" meaning at least 85%, preferably at least 90%. In general, it will be appreciated that the matrix will deliver greater than about 80% of the active agent, preferably at least 85%, preferably greater than 90%, preferably more than 95%, and in certain embodiments 100% of the active agent over a time period in the range of about for example, two to eight hours as determined in vitro using USP disintegration test equipment.

It has now been found that higher molecular weight polymers are preferred to provide a desired extended release profile using the present dosage forms. Suitable molecular weights are generally in the range of about 5,000 to about 20,000,000. For sparingly soluble drugs, the polymers have molecular weights preferably in the range of about 5,000 to about 8,000,000, more preferably in the range of about 10,000 to about 5,000,000. For water-soluble drugs, the polymers preferably have molecular weights of at least about 10,000, but the molecular weight used will vary with the selected polymer. For example, for hydroxypropyl methylcellulose, the minimum molecular weight may be as low as 10,000, while for poly(ethylene oxide)s the molecular weight may be far higher, on the order of 2,000,000 or more.

The benefits of this disclosure will be achieved over a wide range of drug loadings, with the weight ratio of drug to polymer generally, although not necessarily, ranging from 1:1000 to about 85:15, typically from 1:500 to about 85:15, more typically from 1:400 to about 80:20. Preferred loadings (expressed in terms of the weight percent of drug relative to total of drug and polymer) are those within the range of approximately 10% to 80%, more preferably within the range of approximately 30% to 80%, and most preferably, in certain cases, within the range of approximately 30% to 70%. For some applications, however, the benefits will be obtained with drug loadings as low as 0.01%, as may be inferred from the aforementioned ratios.

Such materials include naturally occurring polysaccharides such as chitin, chitosan, dextran and pullulan; gum agar, gum arabic, gum karaya, locust bean gum, gum tragacanth, carrageenans, gum ghatti, guar gum, xanthan gum and scleroglucan; starches such as dextrin and maltodextrin; hydrophilic colloids such as pectin; phosphatides such as lecithin; alginates such as ammonium alginate, sodium, potassium or calcium alginate, propylene glycol alginate; gelatin; collagen; and cellulosics. By "cellulosics" is meant a cellulose polymer that has been modified by reaction of at least a portion of the hydroxyl groups on the saccharide repeat units with a compound to form an ester-linked or an ether-linked substituent. For example, the cellulosic ethyl cellulose has an ether linked ethyl substituent attached to the saccharide repeat unit, while the cellulosic cellulose acetate has an ester linked acetate substituent.

A preferred class of cellulosics for the erodible matrix comprises aqueous-soluble and aqueous-erodible cellulosics such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC). A particularly preferred class of such cellulosics comprises various grades of low viscosity (MW less than or equal to 50,000 daltons) and high viscosity (MW greater than 50,000 daltons) HPMC. Commercially available low viscosity HPMC polymers include the Dow METHOCEL series E5, E5LV, E15LV, E50LV, E50SLV, and K100LY, while high viscosity HPMC polymers include E4MCR, E10MCR, K4M, K15M and K100M; especially preferred in this group are the METHOCEL K series. Other commercially available types of HPMC include the Shin Etsu METOLOSE 90SH series.

Other materials useful as the erodible matrix material include, but are not limited to, pullulan, polyvinyl pyrrolidone, polyvinyl alcohol, polyvinyl acetate, glycerol fatty acid esters, polyacrylamide, polyacrylic acid, copolymers of ethacrylic acid or methacrylic acid (EUDRAGIT®, Rohm America, Inc., Piscataway, N.J.) and other acrylic acid derivatives such as homopolymers and copolymers of butylmethacrylate, methylmethacrylate, ethylmethacrylate, ethylacrylate, (2-dimethylaminoethyl)methacrylate, and (trimethylaminoethyl) methacrylate chloride.

The erodible matrix polymer may contain a wide variety of the same types of additives and excipients known in the pharmaceutical arts, including osmopolymers, osmagens, solubility-enhancing or -retarding agents and excipients that promote stability or processing of the device. In certain embodiments, the at least one erodible matrix material is present in a concentration of about 5% to about 15% w/w of the core. In certain embodiments, the at least one erodible matrix material is present in a concentration of about 1% to about 30% w/w of the core. In certain embodiments, the at least one erodible matrix material is present in a concentration of about 2% to about 25% w/w of the core. In certain embodiments, the at least one erodible matrix material is present in a concentration of about 3% to about 20% w/w of the core. In certain embodiments, the at least one erodible matrix material is present in a concentration of about 10% to about 25% w/w of the core. In certain embodiments, the at least one erodible matrix material is present in a concentration of about 15% to about 25% w/w of the core. In certain embodiments, the at least one erodible matrix material is present in a concentration of about 20% to about 40% w/w of the core. In certain embodiments, the at least one erodible matrix material is present in a concentration of about 21% to about 38% w/w of the core. In certain embodiments, the at least one erodible matrix material is present in a concentration of about 8% to about 13% w/w of the core. In certain embodiments, the at least one erodible matrix material is present in a concentration of about 12.12% w/w of the core. In exemplary embodiments, formulations of the disclosure may comprise erodible matrix material at a concentration of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation, such as the core.

The formulation may comprise an excipient that is a swellable material such as a hydrogel in amounts that can swell and expand. Examples of swellable materials include polyethylene oxide, hydrophilic polymers that are lightly cross-linked, such cross-links being formed by covalent or ionic bond, which interact with water and aqueous biological fluids and swell or expand to some equilibrium state. Swellable materials such as hydrogels exhibit the ability to swell in water and retain a significant fraction of water within its structure, and when cross-linked they will not dissolve in the water. Swellable polymers can swell or expand to a very high degree, exhibiting a 2 to 50 fold volume increase. Specific examples of hydrophilic polymeric materials include poly(hydroxyalkyl methacrylate), poly(N-vinyl-2-pyrrolidone), anionic and cationic hydrogels, polyelectrolyte complexes, poly(vinyl alcohol) having a low acetate residual and cross-linked with glyoxal, formaldehyde, or glutaraldehyde, methyl cellulose cross-linked with dialdehyde, a mixture of cross-linked agar and carboxymethyl cellulose, a water insoluble, water-swellable copolymer produced by forming a dispersion of finely divided copolymer of maleic anhydride with styrene, ethylene, propylene, butylene, or isobutylene cross-linked with from 0.001 to about 0.5 moles of a polyunsaturated cross-linking agent per mole of maleic anhydride in the copolymer, water-swellable polymers of N-vinyl lactams, cross-linked polyethylene oxides, and the like. Other examples of swellable materials include hydrogels exhibiting a cross-linking of 0.05 to 60%, hydrophilic hydrogels known as Carbopol acidic carboxy polymer, Cyanamer™ polyacrylamides, cross-linked water-swellable indene-maleic anhydride polymers, Good-rite™ polyacrylic acid, starch graft copolymers, Aqua-Keeps.™ acrylate polymer, diester cross-linked polyglucan, and the like.

The formulations may comprise additives such as polyethylene oxide polymers, polyethylene glycol polymers, cellulose ether polymers, cellulose ester polymers, homo- and copolymers of acrylic acid cross-linked with a polyalkenyl polyether, poly(meth)acrylates, homopolymers (e.g., polymers of acrylic acid crosslinked with allyl sucrose or allyl pentaerythritol), copolymers (e.g., polymers of acrylic acid and $C_{10}$-$C_{30}$ alkyl acrylate crosslinked with allyl pentaerythritol), interpolymers (e.g., a homopolymer or copolymer that contains a block copolymer of polyethylene glycol and a long chain alkyl acid ester), disintegrants, ion exchange resins, polymers reactive to intestinal bacterial flora (e.g., polysaccharides such as guar gum, inulin obtained from plant or chitosan and chondrotin sulphate obtained from animals or alginates from algae or dextran from microbial origin) and pharmaceutical resins.

A non-limiting list of suitable sustained-release materials which may be included in a sustained-release matrix according to the disclosure includes hydrophilic and/or hydrophobic materials, such as gums, cellulose ethers, acrylic resins, protein derived materials, waxes, shellac, and oils such as hydrogenated castor oil and hydrogenated vegetable oil. However, any pharmaceutically acceptable hydrophobic or hydrophilic sustained-release material which is capable of imparting sustained-release of the API may be used in accordance with the compositions and methods of the disclosure. Preferred sustained-release polymers include alkylcelluloses such as ethylcellulose, acrylic and methacrylic acid polymers and copolymers; and cellulose ethers, especially hydroxyalkylcelluloses (especially hydroxypropylmethylcellulose) and carboxyalkylcelluloses. Preferred acrylic and methacrylic acid polymers and copolymers include methyl methacrylate, methyl methacrylate copolymers, ethoxyethyl methacrylates, ethyl acrylate, trimethyl ammonioethyl methacrylate, cyanoethyl methacrylate, aminoalkyl methacrylate copolymer, poly(acrylic acid), poly(methacrylic acid), methacrylic acid alkylamine copolymer, poly (methylmethacrylate), poly(methacrylic acid) (anhydride), polymethacrylate, polyacrylamide, poly(methacrylic acid anhydride), and glycidyl methacrylate copolymers. Certain preferred embodiments utilize mixtures of any of the foregoing sustained-release materials in the matrix of the disclosure. The matrix also may include a binder.

In addition to the above ingredients, a sustained-release matrix may also contain suitable quantities of other materials, e.g., diluents, lubricants, binders, granulating aids and glidants that are conventional in the pharmaceutical art.

A sustained-release matrix can be prepared by, e.g., melt-granulation or melt-extrusion techniques. Generally, melt-granulation techniques involve melting a normally solid hydrophobic binder material, e.g., a wax, and incorporating a powdered drug therein. To obtain a sustained release dosage form, it may be necessary to incorporate a hydrophobic sustained-release material, e.g., ethylcellulose or a water-insoluble acrylic polymer, into the molten wax hydrophobic binder material.

Colon Specific Drug Delivery

The approaches for colon specific drug delivery system are prodrug or coated or matrix preparation.

The Commonly Used Approaches are:
1. pH dependent
2. Time dependent
3. Pressure dependent
4. Bacteria dependent pH Dependent Delivery:

The change in the pH along the gastrointestinal tract has been used as a mean for colon targeted drug delivery. This can be achieved by means of coating that are intact at lower pH of the stomach but that will dissolved at neutral pH of the colon. The pH in the gastrointestinal tract varies from 1.2 in the stomach, 6.6 in the proximal small intestine and about 7.5 in the distal part of small intestine. This pH variation CSDDS in the stomach and small intestine has previously been used to deliver drugs to small intestine by way of pH sensitive enteric coating. These polymer coats are recalcitrant to the acidic condition of the stomach but ionize and get dissolved above a certain threshold alkaline pH found in small intestine. Thus it is possible to apply same concept to deliver drugs to the terminal of ileum or colon by use of enteric polymers with a relatively high threshold pH for dissolution and subsequent drug release.

The most commonly used polymer for this purpose is methacrylic acid and methylmathacrylate that dissolve at pH 6 (Eudragit L) and pH 7 (Eudragit S) have been investigated. This approach is based on the fact that the gastrointestinal pH is increase progressively from small intestine to colon. But the pH of the distal is 6. This delivery system thus has a inclination to release the drug load prior to reaching the colon. To overcome the problem of premature drug release, a copolymer of methacrylic acid, methyl methacrylate and ethyl acrylate (Eudragit FS) which dissolve at slower rate and at higher threshold pH 7 to 7.5 was reported. The gamma scintigraphic study comparing the in vivo performance of these various polymers revealed that Eudragit FS (coated on tablet) was superior as compare to Eudragit L and S polymers in the terms of drug release retardation in the small intestine. That is the intrasubject variability to this polymer is apparent.

Time Dependent Delivery:

The average transit time in the stomach is 2 hr which may vary, while in the small intestine it is relatively constant around 3 hr. The typical transit time varies from 20 to 30 h. Time dependent drug delivery system allow the drug release after a set time delay. For the colon targeted drug release the lag time should similar to the time taken for the system to reach the colon. The lag time of 5 hr is usually considered sufficient on the basis of relatively constant transit time in the small intestine (3 hr); Pulsicap was the first formulation developed based on this approach.Sinha V R and Kumaria R. demonstrated use of shellac, Eudragit L100 and ethylcellulose at various thicknesses for colon targeted drug delivery of a drug and out of this shellac showed promising result. Time dependent approach was also been used for chronopharmacotherapy using nifedipine and coating with polyethylene oxide-polyethylene glycol mixtures which release the drug in colon. Eudragit L100 along with channeling agent like sodium chloride has been effectively confirmed for achieving colon target drug delivery based on this approach. Hydroxy propyl methyl cellulose has been used for colon specific drug delivery of pseudoephedrine HCL using this approach. Hydroxy propyl ethyl cellulose, Hydroxy propyl methyl cellulose acetate succinate were also been used for time dependent colon specific drug delivery. HPMC along with pectin has also been shown to produce promising result for colon drug delivery system for sennosides which is used as an herbal purgative. The hydrogel based capsule was reported which swells after CSDDS definite time and allow drug release after lag time successfully in colon, hence by modifying hydrogel composition and size, lag time could be varied.

Combination of Time and pH Dependent:

Due to variations in pH and gastric transit time colon drug delivery based only on pH and time would not be consistent. Therefore formulations have been developed base on combination of pH uniqueness of different polymers and transit time in the small intestine using Eudragit FS30D and Eudragit RL-RS32. Pulsatile device in the form of capsule has been developed using this approach for chronopharmacology for better treatment of nocturnal asthma, for example, Krishnamachari Y., et. al. developed a controlled release microparticles of budesonide using poly (dl-lactide-co-glycoside) and Eudragit S-100 based on the combinational Crohn's disease treatment.

Diclofenac sodium and 5-amino salicylic acid pellets were coated with ethylcellulose and methacrylic acid copolymers respectively and in vivo studies using dogs shows promising result of colon targeting following oral administration. Akhgari A., et al, demonstrated combination use of Eudragit S100 and L100 along with Eudragit RS as a single layer coating on pellet for colon targeted drug delivery.

Pressure Dependent Drug Delivery:—

The muscular contraction of the gut generate pressure for grinding and propulsion of intestinal contents, this pressure is vary all the way CSDDS through the gastrointestinal tract, luminal pressure in the colon higher due to the process of stool formation. The pressure controlled delivery consists of drug dispersed in a suppository base, coated with the hydrophobic polymer. On swallowing body temperature causes the melting of suppository base and subsequent increases in volume of the system. The balloon doesn't get rupture in the luminal pressure of the small intestine resulting from muscular contraction, but will rupture when in the colon due to more intense pressure of the contractions of the colon and contents of higher viscosity. Co-administered food may affect the performance of system based on pressure, as fed state contraction may be adequately influential to disintegrate the capsule in the stomach. The empty pressure-controlled colon delivery capsules were developed by a dipping method where the inner coat was water-insoluble polymer membrane like ethylcellulose and the outer one was hydroxypropylmethylcellulose phthalate, an enteric polymer membrane.

Bacteria Dependent Drug Delivery:

Drug can be administered locally and selectively to the colon if they are enclosed in an azo-aromatic cross-linked polymer subject to cleavage by azoreductase of the colonic microflora. This approach of coating a drug with biodegradable material for the colon targeting was reported for used large amount of the drug. The drug release rate is dependent on of the bacterial enzymes activity in the colon rather than on that of the host. The total bacterial count in colon is reported to be 1011 per gram as CSDDS compared to 104 per gram in upper part of gastrointestinal tract, 400 different anaerobic species are present. Azo bond based polymer for the obtaining universal carrier systems was reported but the safety and toxicity of these synthetic polymers need to be considered. Natural materials, fundamentally those that are polysaccharide-based, offer a workable alternative to safety problem, material includes chitosan, amylose, dextran, guar gum, insulin, pectin. Biodegradable polymers degrade in vivo, either in presence of enzyme or nonenzymatically, to produce products which are nontoxic and biocompatible. The microflora composition remains relatively constant across a diverse human population. Amylose one of the polysaccharide obtained from starch shown potential of colonic drug delivery due to degradation of amylase by enzyme amylase in colon. 38. Similarly pectin along with ethylcellulose was reported for colon specific drug delivery of 5-flurouracil. The drug sulfasalazin (SAS) used for IBD40 and rheumatoid arthritis is the earliest example of targeted drug delivery in the colon based on this approach. Only 12% drug was released in the small intestine after oral administration. When SAS reaches the colon after oral administration the diazoreductase bacteria of colon bacteria cleaves the azo bond releasing 5-amino salicylic acid and sulfapyuridine into colon lumen.

Osalazine consist of 5-amino salicylic acid linked by an azo bond was developed to directly deliver 5-amino salicylic acid to the colon. Balsalzide is another prodrug i.e. reported to benefit from a less toxic CSDDS carrier molecule than in SAS. Balasalazide is 5-amino salicylic acid linked by a diazo moiety to 4-amino benzoyl-β-alanine. A comparable total release of 5-amino salicylic acid in rats has been observed from SAS and 5-amino salicylic acid in rat azo linked to polymeric prodrug consisting of polysulfonami-doethylene as a carrier molecule (Polyasa). The prodrug approach has been used where naproxen was conjugated to dextran by an ester linkage. The release of naproxen was higher in the pig caecum and colon homogenates as compare to small intestine. Chitosan, a polysaccharide has been used for colon targeted drug delivery in several dosage forms including, matrices, hydrogel, microspheres and now recently in osmotic pump. Laroyl and crosslinked galactomannan45Cyclodextrins an oligosaccharides46. dextran and amino acid conjugates were successfully reported for colonic drug delivery might be influenced by many factors including diet, drugs, and gastrointestinal diseases may influence the metabolic activities of which should be considered while designing of colon targeted drug delivery system based on this approach.

Combination Therapies

One or more additional agents, such as antipruritic agents, can optionally be used in combination with the active agent of the compositions and methods of the disclosure to treat pruritus (including acute and chronic pruritus). Examples of antipruritic agents include without limitation:

antihistamines, including but not limited to antihistamines that inhibit action at the histamine H.sub.1 receptor (e.g., acrivastine, antazoline, azelastine, bilastine, brompheniramine, buclizine, bromodiphenhydramine, carbinoxamine, cetirizine, chlorpromazine, cyclizine, chlorpheniramine, chlorodiphenhydramine, clemastine, cyproheptadine, desloratadine, dexbrompheniramine, dexchlorpheniramine, dimenhydrinate, dimetindene, diphenhydramine, doxepin, doxylamine, ebastine, embramine, fexofenadine, hydroxyzine, levocetirizine, loratadine, meclozine, mepyramine, mirtazapine, olopatadine, orphenadrine, phenindamine, pheniramine, phenyltoloxamine, promethazine, pyrilamine, quetiapine, rupatadine, tripelennamine and triprolidine), and antihistamines that inhibit action at the histamine H.sub.4 receptor (e.g., thioperamide, JNJ 7777120 and VUF-6002), and analogs and derivatives thereof; serotonin receptor antagonists, including but not limited to 5-HT2 antagonists (e.g., clozapine, cyproheptadine, ketanserin, pizotifen and quetiapine) and 5-HT3 antagonists (e.g., alosetron, cilansetron, dolasetron, granisetron, ondansetron, palonosetron and tropisetron), and analogs and derivatives thereof;

neurokinin-1 (NK-1) receptor antagonists, including but not limited to aprepitant, casopitant (GW679769), dapitant, ezlopitant, fosaprepitant, lanepitant (LY-303870), maropitant, netupitant, nolpitant, orvepitant, rolapitant, vestipitant, vofopitant, AV-818, BIIF 1149CL, CP122,721, DNK-333, GSK-424887, L-733060, L-759274, LY-686017, M516102 and TA-5538, and analogs and derivatives thereof;

opioid receptor antagonists, including but not limited to butorphanol, cyprodime, levallorphan (lorfan or naloxiphan), nalbuphine, nalorphine (lethidrone or nalline), naloxone, naloxol, nalmefene, naltrexone (e.g., naltrexone 1% cream) and naltrexol, and analogs and derivatives thereof;

opioid receptor agonists, including but not limited to selective kappa opioid receptor agonists (e.g., asimadoline, bremazocine, dynorphin, enadoline, ketazocine, nalfurafine, salvinorin A, 2-methoxymethyl salvinorin B, 2-ethoxymethyl salvinorin B, 2-fluoroethoxymethyl salvinorin B, spiradoline, tifluadom, BRL-52537, FE 200665, GR-89696, HZ-2, ICI-199,441, ICI-204,448, LPK-26, U-50488 and U-69,593), and analogs and derivatives thereof;

Janus kinase (JAK) inhibitors, including but not limited to JAK1 inhibitors (e.g., GLPG0634 and GSK2586184), JAK2 inhibitors (e.g., lestaurtinib, pacritinib, CYT387 and TG101348), JAKI/JAK2 inhibitors (e.g., baricitinib and ruxolitinib), and JAK3 inhibitors (e.g., tofacitinib), and analogs and derivatives thereof;

immunomodulators and immunosuppressants, including but not limited to thalidomide, antimetabolites (e.g., antifolates such as methotrexate), and calcineurin inhibitors (e.g., ciclosporin [cyclosporin], pimecrolimus and tacrolimus), and analogs and derivatives thereof; antidepressants, including but not limited to tricyclic antidepressants (e.g., amitriptyline, amitriptylinoxide, amoxapine, dosulepin [dothiepin], doxepin and melitracen), tetracyclic antidepressants (e.g., amoxapine, maprotiline, mazindol, mianserin, mirtazapine and setiptiline), selective serotonin reuptake inhibitors (SSRIs, e.g., citalopram, dapoxetine, escitalopram, fluoxetine, fluvoxamine, paroxetine and sertraline), and serotonin-norepinephrine reuptake inhibitors (SNRIs, e.g., bicifadine, duloxetine, milnacipran, levomilnacipran, sibutramine, venlafaxine, desvenlafaxine and SEP-227162), and analogs and derivatives thereof; anticonvulsants, including but not limited to carbamazepine, gabapentin, pregabalin, and valproic acid and salts thereof (e.g., sodium valproate), and analogs and derivatives thereof;

corticosteroids, including but not limited to hydrocortisone types (e.g., cortisone and derivatives thereof [e.g., cortisone acetate], hydrocortisone and derivatives thereof [e.g., hydrocortisone acetate, hydrocortisone-17-aceponate, hydrocortisone-17-buteprate, hydrocortisone-17-butyrate and hydrocortisone-17-valerate], prednisolone, methylprednisolone and derivatives thereof [e.g., methylprednisolone aceponate], prednisone, and tixocortol and derivatives thereof [e.g., tixocortol pivalate]), betamethasone types (e.g., betamethasone and derivatives thereof [e.g., betamethasone dipropionate, betamethasone sodium phosphate and betamethasone valerate], dexamethasone and derivatives thereof [e.g., dexamethasone sodium phosphate], and fluocortolone and derivatives thereof [e.g., fluocortolone caproate and fluocortolone pivalate]), halogenated steroids (e.g., alclometasone and derivatives thereof [e.g., alclometasone dipropionate], beclometasone and derivatives thereof [e.g., beclometasone dipropionate], clobetasol and derivatives thereof [e.g., clobetasol-17-propionate], clobetasone and derivatives thereof [e.g., clobetasone-17-butyrate], desoximetasone and derivatives thereof [e.g., desoximetasone acetate], diflorasone and derivatives thereof [e.g., diflorasone diacetate], diflucortolone and derivatives thereof [e.g., diflucortolone valerate], fluprednidene and derivatives thereof [e.g., fluprednidene acetate], fluticasone and derivatives thereof [e.g., fluticasone propionate], halobetasol [ulobetasol] and derivatives thereof [e.g., halobetasol proprionate], halometasone and derivatives thereof [e.g., halometasone acetate], and mometasone and derivatives thereof [e.g., mometasone furoate]), acetonides and related substances (e.g., amcinonide, budesonide, ciclesonide, desonide, fluocinonide, fluocinolone acetonide, flurandrenolide [flurandrenolone or fludroxycortide], halcinonide, triamcinolone acetonide and triamcinolone alcohol), and carbonates (e.g., prednicarbate), and analogs and derivatives thereof; local anesthetics, including but not limited to amides (e.g., articaine, bupivacaine, cinchocaine [dibucaine], etidocaine, levobupivacaine, lidocaine [e.g., lidocaine 2.5-5% cream], prilocaine [e.g., prilocaine 2.5% cream], EMLA [lidocaine 2.5%/prilocaine 2.5% cream], mepivacaine, ropivacaine and trimecaine), esters (e.g., benzocaine, chloroprocaine, cocaine, cyclomethycaine, dimethocaine [larocaine], piperocaine, procaine [novocaine], proparacaine, propoxycaine, stovaine and tetracaine [amethocaine]), ethers (e.g., polidocanol [e.g., polidocanol 3% foam] and pramocaine [pramoxine] [e.g., pramoxine 1% cream]), and naturally derived local anesthetics (e.g., cocaine, eugenol, menthol, saxitoxin, neosaxitoxin and tetrodotoxin), and analogs and derivatives thereof; counterirritants and cooling agents, including but not limited to capsaicin, camphor, mint oil, menthol (e.g., menthol 1-3% cream), and phenol (e.g., in calamine lotion), and analogs and derivatives thereof; moisturizers, including but not limited to aqueous moisturizers, low pH moisturizers containing an acid (e.g., lactic acid), and moisturizers containing a humectant that attracts and retains water (e.g., glycerol, sorbitol, lactate, urea, and hyaluronic acid and salts thereof), an occlusive that prevents evaporation {e.g., oils (e.g., mineral oil and silicone oil [e.g., dimethicone]) and petroleum jelly (petrolatum)}, and/or an emollient that provides partial hydration and occlusion (e.g., oils, waxes [e.g., lanolin and paraffin], lipids [e.g., phospholipids, ceramides, triglycerides, glycol stearate, glyceryl stearate, fatty acids and squalene], and sterols [e.g., cholesterol and phytosterol]), and analogs and derivatives thereof; and other kinds of antipruritic agents, including but not limited to S-adenosyl methionine, botulinum toxin (e.g., botulinum toxin types A and B), vitamin D and analogs and derivatives thereof (e.g., calcitriol and calcipotriol [calcipotriene]), non-steroidal anti-inflammatory drugs (NSAIDs, e.g., aspirin), cannabinoid receptor agonists (e.g., $CB_2$ agonists, such as palmitoylethanolamide), inhibitors of cytokines (e.g., antibodies to interleukins, such as IL-31), antagonists of the prostaglandin $0_2$ receptor ($DP_1$) and/or the chemoattractant receptor homologous molecule expressed on $TH_2$ cells (CRTH2) (e.g., TS-022), phosphodiesterase (PDE) inhibitors (e.g., PDE4 inhibitors, such as apremilast), protease-activated receptor 2 (PAR2) antagonists (e.g., GB83), transient receptor potential vanilloid (TRPV) antagonists (e.g., TRPV1 antagonists, such as capsazepine and SB-705498), inhibitors of neurotrophic tyrosine kinase receptors (e.g., TrkA inhibitors, such as CT327), antimicrobials (including antibiotics, antifungals, antivirals and antiparasitics, such as crotamiton and rifampin [rifampicin]), bile absorption-reducing or bile sequestering agents (e.g., ursodeoxycholic acid [ursodiol]), ultraviolet radiation (e.g., ultraviolet A and B), and therapeutic agents that treat the underlying causes of the pruritus-associated conditions, and analogs and derivatives thereof.

If desired (e.g., for relief from pruritus during the day), a non-sedating antipruritic agent can be used. For example, second-generation and third-generation antihistamines are designed to be non-sedating, or less sedating than first-generation antihistamines. Non-limiting examples of second-generation and third-generation antihistamines include acrivastine, astemizole, azelastine, bepotastine, bilastine, cetirizine, levocetirizine, ebastine, fexofenadine, ketotifen, levocabastine, loratadine, desloratadine, mizolastine, olopatadine, quifenadine, rupatadine and terfenadine.

The optional additional antipruritic agent(s) can be administered to a subject suffering from pruritus concurrently with (e.g., in the same composition as the active agent of the disclosure or in separate compositions) or sequentially to (before or after) administration of the active agent of the disclosure. The active agent of the compositions and methods of the disclosure and the optional additional antipruritic agent(s) independently can be administered in any suitable mode, including without limitation orally, topically (e.g., dermally/epicutaneously, transdermally, mucosally, transmucosally, intranasally [e.g., by nasal spray or drop], opthalmically [e.g., by eye drop], pulmonarily [e.g., by inhalation], bucally, sublingually, rectally and vaginally), by injection or infusion (e.g., parenterally, including intramuscularly, subcutaneously, intradermally, intravenously/intravascularly, and intrathecally), and by implantation (e.g., subcutaneously and intramuscularly). In some embodiments, an antipruritic agent is administered topically (e.g., dermally) if the pruritus is localized, and is administered systemically (e.g., orally or intravenously) if the pruritus is widespread (generalized) or has a systemic cause. In certain embodiments, active agent of the disclosure and/or the optional additional antipruritic agent(s) are administered orally. In other embodiments, active agent of the disclosure and/or the optional additional antipruritic agent(s) are administered topically (e.g., dermally, mucosally, bucally or sublingually).

The active agents of the disclosure and the optional additional agent(s), such as antipruritic agents, independently can be administered in any suitable frequency, including without limitation daily (one, two, three or more times per day), every two days, twice weekly, thrice weekly, weekly, every two weeks, every three weeks, monthly, every two months and every three months. The dosing frequency can depend on, e.g., the mode of administration chosen. For example, a dermal formulation of active agent of the disclosure, and/or that of the optional additional antipruritic agent(s), can be applied to the skin of a subject two, three or four times a day. In some embodiments, active agent of the disclosure is administered under a chronic dosing regimen. In certain embodiments, active agent of the disclosure is administered over a period of at least 2 weeks, 3 weeks, 1 month, 1.5 months, 2 months, 3 months, 4 months, 5 months, 6 months or longer.

Coating

The coating of pH-sensitive (enteric) polymers to tablets, capsules and other oral formulations of the present disclosure provided delayed release and protect the active drug from gastric fluid. In general, enteric coatings should be able to withstand the lower pH values of the stomach and small intestine and be able to disintegrate at the neutral or slightly alkaline pH of the large intestine. Enteric coatings are a well-known class of compounds. Coating pharmaceutically active compositions with enteric coatings is well known in the art to enable pharmaceutical compositions to bypass the stomach and its low acidity. Enteric coatings generally refer to a class of compounds that dissolve at or above a particular pH and include a number of pH-sensitive polymers. The pH dependent coating polymer may be selected from those enteric coatings known to those skilled in the art. Such polymers may be one or more of the group comprising hydroxypropylmethylcellulose phthalate, polyvinyl acetate phthalate (PVAP), hydroxypropylmethylcellulose acetate succinate (HPMCAS), alginate, carbomer, carboxymethyl cellulose, methacrylic acid copolymer (such as, for example, a cationic copolymer of dimethyl aminoethyl methacrylate and neutral methacrylic esters), polyvinyl acetate phthalate, cellulose acetate trimellitate, shellac, cellulose acetate phthalate (CAP), starch glycolate, polacrylin, methyl cellulose acetate phthalate, hydroxymethylcellulose phthalate, hydroxymethylmethylcellulose acetate succinate, hydroxypropylcellulose acetate phthalate, cellulose acetate terephthalate, cellulose acetate isophthalate, and includes the various grades of each polymer such as HPMCAS-LF, HPMCAS-MF and HPMCAS-HG, or mixtures thereof. Other enteric coatings suitable for the present disclosure include acetyltributyl citrate, carbomers, guar gum, hypromellose acetate succinate, hypromellose phthalate, polymethacrylates, tributyl citrate, triethyl citrate, white wax, and zein.

In one embodiment, the pH dependent coating is selected from the group consisting of methacrylic acid copolymers of varying threshold pH (such as, but not limited to EUDRAGIT S 100 (a cationic copolymer of dimethyl aminoethyl methacrylate and neutral methacrylic acid esters manufactured by Rohm Pharma GmbH of Darmstadt, Germany)).

Multiple coatings of enteric polymers may be utilized. In one embodiment, the first coating (closest to the core) is an enteric coating that will survive until the dosage form arrives at the large intestine/colon. To target the large intestine, in one embodiment an enteric coating comprises a series of methacrylic acid anionic copolymers known as EUDRAGIT S. The EUDRAGIT S films are colorless, transparent and brittle. In one embodiment, the enteric coating comprises EUDRAGIT S100. The EUDRAGIT S coatings are insoluble in pure water, in buffer solutions below a pH of 6.0 and also in natural and artificial gastric juices. They are slowly soluble in the region of the digestive tract where the juices are neutral to weakly alkaline (i.e., the large intestine and the colon) and in buffer solutions above a pH of 7.0. Mixtures of these various enteric polymers recited above, can be used in the present disclosure. Further, the use of plasticizers is included in one embodiment with the enteric polymer coatings useful herein.

The disintegration rates of enteric coated tablets are dependent on the polymer combination used to coat the tablets, the pH of the disintegration media, and the coating level of the tablets (i.e., thickness of the coating). The presence of plasticizer and the nature of the salts in the dissolution medium also influence the dissolution rate.

The enteric coating may also be modified through the inclusion of an edible acid to retard or slow the dissolution of the coating in the intestines. Any edible acid may be used. Representative edible acids include acetic acid, benzoic acid, fumaric acid, sorbic acid, propionic acid, hydrochloric acid, citric acid, malic acid, tartaric acid, isocitric acid, oxalic acid, lactic acid, the phosphoric acids and mixtures thereof. One embodiment includes fumaric acid and malic acids. The weight percent of the edible acid in the enteric coating solution (polymer, plasticizer, anti-tack agents, water and the like) can range from about 5 to about 40%, with 10 to 30% present in one embodiment and 10 to 25% in another embodiment. Those skilled in the art will readily be able to determine the exact amount of edible acid to include in the coating solution, depending upon the pKa of the particular edible acid and the desired delay in dissolution of the enteric coating. After application of the enteric coating solution, as further described below, the percent of edible acid in the coating will range from about 10 to about 80 weight % of the coating; 20 to 60% in one embodiment; and 25-50% in another.

Enteric coatings can be obtained from a number of manufacturers, such as, for example, Rohm Pharma GmbH of Darmstadt, Germany (EUDRAGIT). Particular blends of pH sensitive polymers and types can be selected by one of skill in the art. As an example, the manufacturer of EUDRAGIT polymers teaches that the EUDRAGIT grades for sustained release formulations are based on copolymers of acrylate and methacrylates with quaternary ammonium groups as functional groups as well as ethylacrylate methylmethacrylate copolymers with a neutral ester group. EUDRAGIT polymers are available insoluble and/or permeable. For example, the EUDRAGIT RL-types are highly permeable, the EUDRAGIT RS-types are poorly permeable, the EUDRAGIT NE-types are swellable and permeable. The release profiles and locations of release can be determined by varying mixing ratios of the polymers and/or film thickness of the coatings and such profiles can be adjusted by those of skill in the art.

The amount of enteric coating is, in one embodiment about 0.1% of the formulation, such as the drug core, about 0.2% of the formulation, such as the drug core, about 0.3% of the formulation, such as the drug core, about 0.4% of the formulation, such as the drug core, about 0.5% of the formulation, such as the drug core, about 0.6% of the formulation, such as the drug core, about 0.7% of the formulation, such as the drug core, about 0.8% of the formulation, such as the drug core, about 0.9% of the formulation, such as the drug core, about 1% w/w of the formulation, such as the drug core; about 2%, w/w of the formulation, such as the drug core, about 3%, w/w, of the formulation, such as the drug core, about 4%, w/w, of the formulation, such as the drug core; about 5% w/w of the formulation, such as the drug core; about 6%, w/w of the formulation, such as the drug core; about 7%, w/w, of the formulation, such as the drug core, about 8%, w/w, of the formulation, such as the drug core; about 9% w/w of the formulation, such as the drug core; about 10%, w/w of the formulation, such as the drug core, about 11%, w/w, of the formulation, such as the drug core, about 12%, w/w, of the formulation, such as the drug core; about 14% w/w of the formulation, such as the drug core; about 16%, w/w of the formulation, such as the drug core, about 18%, w/w, of the formulation, such as the drug core, about 20%, w/w, of the formulation, such as the drug core; or more, if determined to be appropriate. Seal coats may also be applied at amounts between about 1% and about 10% w/w of the formulation, such as the drug core, between about 2% and 9% w/w of the formulation, such as the drug core, between about 3% and 8% w/w of the formulation, such as the drug core, between about 4% and 7% w/w of the formulation, such as the drug core, between about 10% and 10% w/w of the formulation, such as the drug core, and between about 5% and about 6% w/w of the formulation, such as the drug core.

In some embodiments, coatings include those that selectively dissolve at a pH at or above the pH generally prevailing in the large intestine, for example, above about pH 6, above about pH 6.2, above about pH 6.4, above about pH 6.6, above about pH 6.8, or above about pH 7. In one embodiment, the enteric coating will selectively dissolve in the pH range of about 6.0 to about 7.5, in the pH range of about 6.2 to about 7.5, in the pH range of about 6.4 to about 7.2, in the pH range of about 6.5 to about 7, in the pH range of about 6.5 to 6.8. As an example of coatings and their "threshold" pH (the pH at which the coating will dissolve) which the skilled practitioner may consider include, but are not limited to, cellulose phthalates (e.g., hydropropylmethylcellulose phthalates (HPMCPs)) that selectively dissolve at pH above 5.6, the EUDRAGIT family of polymers which are anionic polymer based on methacrylic acid and methacrylates with carboxyl functional groups (e.g., EUDRAGIT L30D with threshold pH of 5.6, EUDRAGIT L with threshold pH of 6.0, and EUDRAGIT S with threshold pH of 6.8), AQUATERIC with threshold pH of 5.8, polyvinylacetate phthalate (PVAP) that releases drug at pH values above about 5.0, shellac that is obtained from a gummy exudation produced by female insects, Laccifer lacca ken, and releases drug at about pH 7.0, and cellulose acetate phthalate (CAP) with threshold pH of 6.0. In a one embodiment, the drug is enteric-coated with EUDRAGIT S100 with threshold pH of 7.0, which will degrade measurably at slightly lower pH such as pH 6.8.

In one embodiment, prior to application to the tablets, capsules, or drug core of the present disclosure, the drug release controlling component, such as, for example, the enteric coatings useful in the present disclosure, will be dissolved in a non-aqueous solution in order to create the solid oral formulation of the present disclosure. Examples of such non aqueous solutions include any known in the art suitable for pharmaceutical formulation procedures, including, for example, acetone-isopropanol solvent mixtures, methylene chloride-ethanol solvent mixtures, acetone-ethanol solvent mixtures, benzene-methanol solvent mixtures, acetate-ethanol solvent mixtures, among others. Proportions of each solvent to use and conditions will be readily determined by those of skill in the art. The solid dispersion of the composition of the present disclosure, in one embodiment, can be formed by spray drying techniques, although it will be understood that suitable solid dispersions may be formed by a skilled addressee utilizing other conventional techniques, such as co-grinding, melt extrusion, freeze drying, rotary evaporation or any solvent removal process. In one embodiment, spray drying is utilized. The enteric coating may be applied over the entire surface area or portions thereof. In one embodiment, the entire surface area is coated.

In one embodiment, the enteric coat comprises EUDRAGIT S100 and the amount of enteric coat to use, relative to the drug core, or additional to the drug core, an amount of about 0.1% of the drug core, about 0.2% of the drug core, about 0.3% of the drug core, about 0.4% of the drug core, about 0.5% of the drug core, about 0.6% of the drug core, about 0.7% of the drug core, about 0.8% of the drug core, about 0.9% of the drug core, about 1% w/w of the drug core, about 2% w/w of the drug core; about 3% w/w of the drug core; about 4%, w/w of the drug core, about 5% w/w of the drug core; about 6%, w/w, of the drug core, about 7% w/w of the drug core, about 8%, w/w, of the drug core; about 9% w/w of the drug core, about 10% w/w of the drug core; about 12%, w/w of the drug core; about 14%, w/w, of the drug core, about 16%, w/w/, of the drug core; about 18% w/w of the drug core; about 20% w/w of the drug core, about 22%, w/w, of the drug core, about 24%, w/w, of the drug core; about 26% w/w of the drug core; about 28%, w/w of the drug core, about 30%, w/w, of the drug core, about 32%, w/w, of the drug core; about 34% w/w of the drug core; about 36%, w/w of the drug core, about 38%, w/w, of the drug core, about 40%, w/w, of the drug core; about 42% w/w of the drug core; about 44%, w/w of the drug core; about 46%, w/w, of the drug core, about 48%, w/w/, of the drug core; about 50% w/w of the drug core; about 52%, w/w of the drug core, about 54%, w/w, of the drug core, about 56%, w/w, of the drug core; about 58% w/w of the drug core; about 60%, w/w of the drug core, about 62%, w/w, of the drug core, about 64%, w/w, of the drug core; about 66% w/w of the drug core; about 68%, w/w of the drug core, about 70%, w/w, of the drug core, about 72%, w/w, of the drug core; about 74% w/w of the drug core; about 76%, w/w of the drug core; about 78%, w/w, of the drug core, about 80%, w/w/, of the drug core; about 82% w/w of the drug core; about 84%, w/w of the drug core, about 86%, w/w, of the drug core, about 88%, w/w, of the drug core; about 90% w/w of the drug core; about 92%, w/w of the drug core, about 91%, w/w, of the drug core, about 96%, w/w, of the drug core; about 98%, w/w, of the drug core, or more, if determined to be appropriate. Ranges include between about 2% and about 20% w/w of the formulation; between about 3% and about 15% w/w of the formulation; between about 4% and about 10% w/w of the formulation; between about 5% and about 9% w/w of the formulation; between about 6% and about 8% w/w of the formulation.

Administration

A composition containing a bile acid sequestrant (e.g., colesevelam) can be administered to a mammal in any amount, at any frequency, and for any duration effective to achieve a desired outcome (e.g., to treat diarrhea). In some cases, a composition containing a bile acid sequestrant can be administered to a mammal to reduce colonic transit by 10, 11, 12, 13, 14, 15, 16, 17, 18, 19, 20, 25, 30, 35, 40, 45, 50, 55, 60, 65, 70 percent or more). An effective amount of a composition containing a bile acid sequestrant can be any amount that reduces a mammal's diarrhea without producing significant toxicity to a mammal Typically, an effective amount of a composition containing a bile acid sequestrant can be any amount greater than or equal to about 200 mg of a bile acid sequestrant (e.g., greater than or equal to about 200 mg, about 250 mg, about 500 mg, about 600 mg, about 650 mg, about 750 mg, about 1000 mg, about 1250 mg, about 1500 mg, about 1750 mg, about 2000 mg, or more of, for example, colesevelam per administration) provided that that amount does not induce significant toxicity to the mammal upon administration. In some cases, an effective amount of a bile acid sequestrant, such as colesevelam, can be between 250 mg and 10 g (e.g., between 250 mg and 1250 mg, between 500 mg and 1500 mg, or between 750 mg and 2000 mg). Various factors can influence the actual effective amount used for a particular application. For example, the frequency of administration, duration of treatment, use of multiple treatment agents, route of administration, and severity of the diarrhea may require an increase or decrease in the actual effective amount administered.

The frequency of administration of a composition containing a bile acid sequestrant can be any frequency that reduces a mammal's diarrhea without producing significant toxicity to the mammal. For example, the frequency of administration can be from about three times a day to about twice a week (e.g., once a day). The frequency of administration can remain constant or can be variable during the duration of treatment. For example, a composition containing a bile acid sequestrant can be administered daily, twice a day, three times a day, five days a week, or three days a week. A composition containing a bile acid sequestrant can be administered for five days, 10 days, three weeks, four weeks, eight weeks, 48 weeks, one year, 18 months, two years, three years, or five years. A course of treatment can include rest periods. For example, a composition containing a bile acid sequestrant can be administered for five days followed by a ten-day rest period, and such a regimen can be repeated multiple times. As with the effective amount, various factors can influence the actual frequency of administration used for a particular application. For example, the effective amount, duration of treatment, use of multiple treatment agents, route of administration, and severity of the diarrhea may require an increase or decrease in administration frequency.

An effective duration for administering a composition containing a bile acid sequestrant can be any duration that reduces a mammal's diarrhea without producing significant toxicity to the mammal. Thus, the effective duration can vary from several days to several weeks, months, or years. In general, the effective duration for the treatment of diarrhea can range in duration from one day to several days to several months. In some cases, an effective duration can be for as long as an individual mammal is alive and suffering from diarrhea. Multiple factors can influence the actual effective duration used for a particular treatment. For example, an effective duration can vary with the frequency of administration, effective amount, use of multiple treatment agents, route of administration, and severity of the diarrhea.

Lubricant

In exemplary embodiments, the pharmaceutical composition of the disclosure may include lubricants such as talc, calcium stearate, magnesium stearate, solid polyethylene glycols, sodium lauryl sulfate, and mixtures thereof and other tableting aids such a magnesium stearate and microcrystalline cellulose The pharmaceutical compositions disclosed herein may also further comprise at least one lubricant, which facilitates preparation of solid dosage forms of the pharmaceutical composition. Non-limiting examples of suitable lubricants include magnesium stearate, calcium stearate, zinc stearate, colloidal silicon dioxide, hydrogenated vegetable oils, sterotex, polyoxyethylene monostearate, polyethylene glycol, sodium stearyl fumarate, sodium benzoate, sodium lauryl sulfate, magnesium lauryl sulfate, and light mineral oil. In exemplary embodiments, the lubricant may be magnesium stearate.

In embodiments in which the lubricant is included in the pharmaceutical composition, the amount of the lubricant may range from about 0.1% to about 3% by weight of the pharmaceutical composition. In various embodiments, the amount of the lubricant may range from about 0.1% to about 4% w/w, from about 0.3% to about 3% w/w, from about 0.4% to about 2% w/w, or from about 1% to about 3% w/w by weight of the pharmaceutical composition. In exemplary embodiments, the amount of the lubricant may be about 1% by weight of the pharmaceutical composition, such as the core or total formulation. In exemplary embodiments, the lubricant may be present at a concentration of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% of the formulation.

Disintegrants

Disintegrants are used to facilitate disintegration of the tablet, thereby increasing the erosion rate relative to the dissolution rate, and are generally starches, clays, celluloses, algins, gums, or crosslinked polymers (e.g., crosslinked polyvinyl pyrrolidone). Fillers include, for example, materials such as silicon dioxide, titanium dioxide, alumina, talc, kaolin, powdered cellulose, and microcrystalline cellulose, as well as soluble materials such as mannitol, urea, sucrose, lactose, lactose monohydrate, dextrose, sodium chloride, and sorbitol. Solubility-enhancers, including solubilizers per se, emulsifiers, and complexing agents (e.g., cyclodextrins), may also be advantageously included in the present formulations. Stabilizers, as well known in the art, are used to inhibit or retard drug decomposition reactions that include, by way of example, oxidative reactions. In various embodiments, the amount of the disintegrant may range from about 0.1% to about 4% w/w, from about 0.3% to about 3% w/w, from about 0.4% to about 2% w/w, or from about 1% to about 3% w/w by weight of the pharmaceutical composition. Disintegrants may be present in a concentration of, for example, from about 0.25 wt. % to about 3 wt. %, 0.5 wt. % to about 2.0 wt. %, from about 0.75% to about 1.5% w/w of the formulation. In exemplary embodiments, the disintegrant may be present at a concentration of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% of the formulation.

Coating

The pharmaceutical composition can be coated with one or more enteric coatings, seal coatings, film coatings, barrier coatings, compress coatings, fast disintegrating coatings, or enzyme degradable coatings.

Delayed release generally refers to the delivery so that the release can be accomplished at some generally predictable location in the lower intestinal tract more distal to that which would have been accomplished if there had been no delayed release alterations. A preferred method for delay of release is coating. Any coatings should be applied to a sufficient thickness such that the entire coating does not dissolve in the gastrointestinal fluids at pH below about 5, but does dissolve at pH about 5 and above. It is expected that any enteric coating in the practice of the compositions and methods of the disclosure to achieve delivery to the lower gastrointestinal tract, such as the large intestine and/or colon.

In some cases, the formulation disclosed herein is coated with a coating material, e.g., a sealant. In some embodiments, the coating material is water soluble. In some embodiments, the coating material comprises a polymer, plasticizer, a pigment, or any combination thereof. In some embodiments, the coating material is a form of a film coating, e.g., a glossy film, a pH independent film coating, an aqueous film coating, a dry powder film coating (e.g., complete dry powder film coating), or any combination thereof. In some embodiments, the coating material is highly adhesive. In some embodiments, the coating material provides low level of water permeation. In some embodiments, the coating material provides oxygen barrier protection. In some embodiments, the coating material allows immediate disintegration for fast release of drug actives. In some embodiments, the coating material is pigmented, clear, or white. In some embodiments, the coating material is clear. Exemplary coating materials include, without limitation, polyvinyl alcohol (PVA), cellulose acetate phthalate (CAP), polyvinyl acetate phthalate (PVAP), methacrylic acid copolymers, cellulose acetate trimellitate (CAT), hydroxypropyl methylcellulose phthalate (HPMCP), hydroxypropyl methylcellulose (HPMC), hydroxy propyl methyl cellulose acetate succinate (hypromellose acetate succinate), shellac, sodium alginate, and zein. In some embodiments, the coating material comprises or is PVA. In some embodiments, the coating material comprises or is HPMC. An exemplary PVA-based coating material includes Opadry II. In some instances, the coating material is about 1, 2, 3, 4, 5, 6, 7, 8, 9, or 10% of the weight of the formulation.

In some instances, the coating material represent between about 1% and about 15% of the total weight of each first particulate, including, but not limited to, between about 5% and about 10%, between about 6% and about 10%, between about 7% and about 10%, between about 8% and about 10%, or between about 9% and about 10% of the formulation. In some instances, the coating material is greater than about 2%, greater than about 3%, greater than about 4%, greater than about 5%, greater than about 6%, greater than about 7%, greater than about 8%, greater than about 9%, or greater than about 10% of the weight of the formulation. In some instances, the coating material is less than about 2%, less than about 3%, less than about 4%, less than about 5%, less than about 6%, less than about 7%, less than about 8%, less than about 9%, or less than about 10% of the weight of the formulation. In exemplary embodiments, the coating may be present at a concentration of about 0.1% of the drug core, about 0.2% of the drug core, about 0.3% of the drug core, about 0.4% of the drug core, about 0.5% of the drug core, about 0.6% of the drug core, about 0.7% of the drug core, about 0.8% of the drug core, about 0.9% of the drug core, about 1% w/w of the drug core, about 2% w/w of the drug core; about 3% w/w of the drug core; about 4%, w/w of the drug core, about 5% w/w of the drug core; about 6%, w/w, of the drug core, about 7% w/w of the drug core, about 8%, w/w, of the drug core; about 9% w/w of the drug core, about 10% w/w of the drug core; about 12%, w/w of the drug core; about 14%, w/w, of the drug core, about 16%, w/w/, of the drug core; about 18% w/w of the drug core; about 20%, w/w of the drug core, about 22%, w/w, of the drug core, about 24%, w/w, of the drug core; about 26% w/w of the drug core; about 28%, w/w of the drug core, about 30%, w/w, of the drug core, about 32%, w/w, of the drug core; about 34% w/w of the drug core; about 36%, w/w of the drug core, about 38%, w/w, of the drug core, about 40%, w/w, of the drug core; about 42% w/w of the drug core; about 44%, w/w of the drug core; about 46%, w/w, of the drug core, about 48%, w/w/, of the drug core; about 50% w/w of the drug core; about 52%, w/w of the drug core, about 54%, w/w, of the drug core, about 56%, w/w, of the drug core; about 58% w/w of the drug core; about 60%, w/w of the drug core, about 62%, w/w, of the drug core, about 64%, w/w, of the drug core; about 66% w/w of the drug core; about 68%, w/w of the drug core, about 70%, w/w, of the drug core, about 72%, w/w, of the drug core about 74% w/w of the drug core; about 76%, w/w, of the drug core; about 78%, w/w, of the drug core, about 80%, w/w/, of the drug core; about 82% w/w of the drug core; about 84%, w/w of the drug core, about 86%, w/w, of the drug core, about 88%, w/w, of the drug core; about 90% w/w of the drug core; about 92%, w/w of the drug core, about 91%, w/w, of the drug core, about 96%, w/w, of the drug core; about 98%, w/w, of the drug core, or more, if determined to be appropriate. Ranges include between about 2% and about 20% w/w of the formulation; between about 3% and about 15% w/w of the formulation; between about 4% and about 10% w/w of the formulation; between about 5% and about 9% w/w of the formulation; between about 6% and about 8% w/w of the formulation.

The compositions of the disclosure can be coated with one or more enteric coatings, seal coatings, film coatings, barrier coatings, compress coatings, fast disintegrating coatings, or enzyme degradable coatings. Multiple coatings can be applied for desired performance. Further, the dosage form can be designed for immediate release, pulsatile release, controlled release, extended release, delayed release, targeted release, synchronized release, or targeted delayed release. For release control, solid carriers can be made of various component types and levels or thicknesses of coats, with or without an active ingredient. Such diverse solid carriers can be blended in a dosage form to achieve a desired performance. The definitions of these terms are known to those skilled in the art. In addition, the dosage form release profile can be affected by a polymeric matrix composition, a coated matrix composition, a multiparticulate composition, a coated multiparticulate composition, an ion-exchange resin-based composition, an osmosis-based composition, or a biodegradable polymeric composition. Without wishing to be bound by theory, it is believed that the release may be effected through favorable diffusion, dissolution, erosion, ion-exchange, osmosis or combinations thereof.

When formulated as a capsule, the capsule can be a hard or soft gelatin capsule, a starch capsule, or a cellulosic capsule. Although not limited to capsules, such dosage forms can further be coated with, for example, a seal coating, an enteric coating, an extended release coating, or a targeted delayed release coating. These various coatings are known in the art, but for clarity, the following brief descriptions are provided: seal coating, or coating with isolation layers: Thin layers of up to 20 microns in thickness can be applied for variety of reasons, including for particle porosity reduction, to reduce dust, for chemical protection, to mask taste, to reduce odor, to minimize gastrointestinal irritation, etc. The isolating effect is proportional to the thickness of the coating. Water soluble cellulose ethers are preferred for this application. HPMC and ethyl cellulose in combination, or EUDRAGIT® E100, may be particularly suitable for taste masking applications. Traditional enteric coating materials listed elsewhere can also be applied to form an isolating layer.

Extended or delayed release coatings are designed to effect delivery over an extended period of time. The extended or delayed release coating is a pH-independent coating formed of, for example, ethyl cellulose, hydroxypropyl cellulose, methylcellulose, hydroxymethyl cellulose, hydroxyethyl cellulose, acrylic esters, or sodium carboxymethyl cellulose. Various extended or delayed release dosage forms can be readily designed by one skilled in art to achieve delivery to both the small and large intestines, to only the small intestine, or to only the large intestine, depending upon the choice of coating materials and/or coating thickness.

Enteric coatings are mixtures of acceptable excipients which are applied to, combined with, mixed with or otherwise added to the carrier or composition. The coating may be applied to a compressed or molded or extruded tablet, a gelatin capsule, and/or pellets, beads, granules or particles of the carrier or composition. The coating may be applied through an aqueous dispersion or after dissolving in appropriate solvent.

Dosage forms of the compositions of the present disclosure can also be formulated as enteric coated delayed release oral dosage forms, i.e., as an oral dosage form of a composition as described herein which utilizes an enteric coating to affect release in the lower gastrointestinal tract. The enteric coated dosage form may be a compressed or molded or extruded tablet/mold (coated or uncoated) containing granules, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

Delayed release coating compositions comprise a polymeric material, e.g., cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, polymers and copolymers formed from acrylic acid, methacrylic acid, and/or esters thereof. Preferred enteric coatings herein are comprised of methacrylic acid copolymers, types A, B, or C, which are commercially available from Rohm Tech, Inc. (Malden, Mass.), and water-based dispersions of cellulose acetate phthalate latex, which is commercially available from Eastman Fine Chemicals (Kingsport, Tenn.).

Plasticizers can also be included in the tablets to modify the properties and characteristics of the polymers used in the coats or core of the tablets. As used herein, the term "plasticizer" includes all compounds capable of plasticizing or softening a polymer or binder used in compositions and methods of the disclosure. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the disclosure.

Plasticizers useful in the compositions and methods of the disclosure can include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the disclosure, that a combination of plasticizers may be used in the present formulation. The PEG based plasticizers are available commercially or can be made by a variety of methods, such as disclosed in *Poly(ethylene glycol) Chemistry: Biotechnical and Biomedical Applications* (J. M. Harris, Ed.; Plenum Press, NY) the disclosure of which is hereby incorporated by reference.

In certain embodiments, the plasticizer is present in a concentration of about 0.5% to about 2% w/w of the outer coating. In certain embodiments, the plasticizer is present in a concentration of about 0.75% to about 1% w/w of the outer coating. In certain embodiments, the plasticizer is present in a concentration of about 0.87% w/w of the outer coating.

The external coat can be applied as a compression coating, but it is generally applied as a sprayed coating. The sprayed coating is thinner and lighter than the compression coating, and an osmotic device including the sprayed on external coating is, therefore, smaller than a similar osmotic device having a compression coat. Moreover, the use of a sprayed-on drug-containing water soluble coating permits the loading of higher amounts of drug than the use of a compression-coated drug-containing water soluble coating. A smaller size osmotic device generally results in increased patient compliance in taking the osmotic device and is therefore advantageous.

The tablets of the disclosure can be coated with a finish coat as is commonly done in the art to provide the desired shine, color, taste or other aesthetic characteristics. Materials suitable for preparing the finish coat are well known in the art and found in the disclosures of many of the references cited and incorporated by reference herein.

Multiple coatings can be applied for desired performance. Further, the dosage form can be designed for immediate release, pulsatile release, controlled release, extended release, delayed release, targeted release, synchronized release, or targeted delayed release. For release/absorption control, solid carriers can be made of various component types and levels or thicknesses of coats, with or without an active ingredient. Such diverse solid carriers can be blended in a dosage form to achieve a desired performance. The definitions of these terms are known to those skilled in the art. In addition, the dosage form release profile can be affected by a polymeric matrix composition, a coated matrix composition, a multiparticulate composition, a coated multiparticulate composition, an ion-exchange resin-based composition, an osmosis-based composition, or a biodegradable polymeric composition. Without wishing to be bound by theory, it is believed that the release may be effected through favorable diffusion, dissolution, erosion, ion-exchange, osmosis or combinations thereof.

Dosage forms of the compositions and methods of the disclosure can further be coated with, for example, a seal coating, an enteric coating, an extended release coating, or a targeted delayed release coating. These various coatings are known in the art, but for clarity, the following brief descriptions are provided: seal coating, or coating with isolation layers: Thin layers of up to 20 microns in thickness can be applied for variety of reasons, including for particle porosity reduction, to reduce dust, for chemical protection, to mask taste, to reduce odor, to minimize gastrointestinal irritation, etc. The isolating effect is proportional to the thickness of the coating. Water soluble cellulose ethers are preferred for this application. HPMC and ethyl cellulose in combination, or Eudragit E100, may be particularly suitable. In exemplary embodiments, the coating may be OPADRY® Y-1-7000, a coating ready mix from Colorcon. Opadry Y-1-7000 contains hypromellose 5 cP, titanium dioxide and macrogol/PEG 400; Shin-Etsu AQOAT® (hypromellose acetate succinate); COLORCOAT® FC4S which is Hydroxypropyl methyl cellulose. Traditional enteric coating materials listed elsewhere can also be applied to form an isolating layer.

Optionally, the sustained-release matrix multiparticulate systems, tablets, or capsules can be coated with a sustained release coating such as the sustained release coatings described herein. Such coatings preferably include a sufficient amount of hydrophobic and/or hydrophilic sustained-release material to obtain a weight gain level from about 2 to about 25 percent, although the overcoat may be greater depending upon, e.g., the desired release rate. In certain embodiments, a sustained release coating is applied to the sustained release spheroids, granules, or matrix multiparticulates. In such embodiments, the sustained-release coating may include a water insoluble material such as (a) a wax, either alone or in admixture with a fatty alcohol; or (b) shellac or zein. The coating is preferably derived from an aqueous dispersion of the hydrophobic sustained release material.

In other preferred embodiments of the present compositions and methods of the disclosure, the sustained release material comprising the sustained-release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers Ammonio methacrylate copolymers are well known in the art as fully polymerized copolymers of acrylic and methacrylic acid esters with a low content of quaternary ammonium groups. In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present disclosure. For example, there are a family of copolymers synthesized from diethylaminoethyl methacrylate and other neutral methacrylic esters, also known as methacrylic acid copolymer or polymeric methacrylates, commercially available as Eudragit® from Rohm GMBH and Co. Kg Darmstadt, Germany. There are several different types of Eudragit®. For example, Eudragit E is an example of a methacrylic acid copolymer which swells and dissolves in acidic media. Eudragit L is a methacrylic acid copolymer which does not swell at about pH<5.7 and is soluble at about pH>6. Eudragit S does not swell at about pH<6.5 and is soluble at about pH>7. Eudragit RL and Eudragit RS are water swellable, and the amount of water absorbed by these polymers is pH-dependent; however, dosage forms coated with Eudragit RL and RS are pH-independent.

In certain preferred embodiments, the acrylic coating comprises a mixture of two acrylic resin lacquers commercially available under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

Examples of suitable plasticizers include water insoluble plasticizers such as dibutyl sebacate, diethyl phthalate, triethyl citrate, tributyl citrate, and triacetin, acetylated monoglycerides, diacylated monoglyceride, phthalate esters, castor oil, and combinations thereof, etc. may be used. Acetylated monoglycerides is an especially preferred plasticizer for the disclosure.

Extended release coatings are designed to effect delivery over an extended period of time. The extended release coating is a pH-independent coating formed of, for example, ethyl cellulose, hydroxypropyl cellulose, methylcellulose, hydroxymethyl cellulose, hydroxyethyl cellulose, acrylic esters, or sodium carboxymethyl cellulose. Various extended release dosage forms can be readily designed by one skilled in art to achieve delivery to both the small and large intestines, to only the small intestine, or to only the large intestine, depending upon the choice of coating materials and/or coating thickness.

Enteric coatings are mixtures of pharmaceutically acceptable excipients which are applied to, combined with, mixed with or otherwise added to the carrier or composition. The coating may be applied to a compressed or molded or extruded tablet, a gelatin capsule, and/or pellets, beads, granules or particles of the carrier or composition. The coating may be applied through an aqueous dispersion or after dissolving in appropriate solvent.

In certain embodiments, the pharmaceutical composition, upon oral administration to a human or non-human patient in need thereof, provides controlled release for at least about 1, 2, 3, 4, 5, 6, 7, 8, 9, 10, 11, 12, 14, 16, 18, 20, 24, 36, 48, 72, 96, 120, 144, or 168 hours.

The term "sustained release" refers release of a drug from its dosage form (e.g., tablet) at such a rate that its blood levels are maintained within the therapeutic range (i.e., at or above minimum effective concentration (MEC)) but below toxic levels over an extended period of time (e.g., about 1, 2, 3, 4, 5, 6, 7, 8, 9, 10, 11, 12, 14, 16, 18, 20, 22, 24, 36, 48, 72, 96, 120, 144, or 168 hours or greater). The term "sustained release" may be used interchangeably with "slow-release," "controlled release," or "extended release." The sustained release property of a dosage form is typically measured by an in vitro dissolution method and confirmed by an in vivo blood concentration-time profile (i.e., a pharmacokinetic profile).

In certain embodiments, the pharmaceutical compositions of the present disclosure release about 90% to 100% of their pharmaceutically active agents in a linear or near linear fashion for at least about 1, 2, 3, 4, 5, 6, 7, 8, 9, 10, 11, 12, 13, 14, 15, 16, 17, 18, 19, 20, 21, 22, 23, 24, 36, 48, 72, 96, 120, 144, or 168 hours in an in vitro dissolution analysis.

Delayed release generally refers to the delivery so that the release can be accomplished at some generally predictable location in the lower intestinal tract more distal to that which would have been accomplished if there had been no delayed release alterations. The preferred method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present disclosure to achieve delivery to the lower gastrointestinal tract. Polymers for use in the present disclosure are anionic carboxylic polymers.

In exemplary embodiments, the coating may comprise shellac, also called purified lac, a refined product obtained from the, resinous secretion of an insect. This coating dissolves in media of pH>7.

Colorants, detackifiers, surfactants, antifoaming agents, lubricants, stabilizers such as hydroxy propyl cellulose, acid/base may be added to the coatings besides plasticizers to solubilize or disperse the coating material, and to improve coating performance and the coated product.

Dosage Forms

The compositions of the present disclosure can provided in the form of a minicapsule, a capsule, a tablet, an implant, a troche, a lozenge (minitablet), a temporary or permanent suspension, an ovule, a suppository, a wafer, a chewable tablet, a quick or fast dissolving tablet, an effervescent tablet, a granule, a film, a sprinkle, a pellet, a bead, a pill, a powder, a triturate, a platelet, a strip or a sachet. Compositions can also be administered after being mixed with, for example yoghurt or fruit juice and swallowed or followed with a drink or beverage. These forms are well known in the art and are packaged appropriately. The compositions can be formulated for oral or rectal delivery.

Tablets prepared for oral administration according to the disclosure, and manufactured using direct compression, will generally contain other inactive additives such as binders, lubricants, disintegrants, fillers, stabilizers, surfactants, coloring agents, and the like. Binders are used to impart cohesive qualities to a tablet, and thus ensure that the tablet remains intact after compression. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate ( ) calcium stearate, stearic acid, and hydrogenated vegetable oil (preferably comprised of hydrogenated and refined triglycerides of stearic and palmitic acids at about 1 wt. % to 5 wt. %, most preferably less than about 2 wt. %). Lubricants may be present in a concentration of, for example, from about 0.25 wt. % to about 3 wt. %, 0.5 wt. % to about 2.0 wt. %, from about 0.75% to about 1.5%.

Disintegrants are used to facilitate disintegration of the tablet, thereby increasing the erosion rate relative to the dissolution rate, and are generally starches, clays, celluloses, algins, gums, or crosslinked polymers (e.g., crosslinked polyvinyl pyrrolidone). Fillers include, for example, materials such as silicon dioxide, titanium dioxide, alumina, talc, kaolin, powdered cellulose, and microcrystalline cellulose, as well as soluble materials such as mannitol, urea, sucrose, lactose, lactose monohydrate, dextrose, sodium chloride, and sorbitol. Solubility-enhancers, including solubilizers per se, emulsifiers, and complexing agents (e.g., cyclodextrins), may also be advantageously included in the present formulations. Stabilizers, as well known in the art, are used to inhibit or retard drug decomposition reactions that include, by way of example, oxidative reactions. Disintegrants may be present in a concentration of, for example, from about 0.25 wt. % to about 3 wt. %, 0.5 wt. % to about 2.0 wt. %, from about 0.75% to about 1.5%.

Shellac, also called purified lac, a refined product obtained from the, resinous secretion of an insect. This coating dissolves in media of pH>7.

Colorants, detackifiers, surfactants, antifoaming agents, lubricants, stabilizers such as hydroxy propyl cellulose, acid/base may be added to the coatings besides plasticizers to solubilize or disperse the coating material, and to improve coating performance and the coated product.

In carrying out the method of the present disclosure, the combination of the disclosure may be administered to mammalian species, such as dogs, cats, humans, etc. and as such may be incorporated in a conventional systemic dosage form, such as a tablet, capsule, or elixir. The above dosage forms will also include the necessary carrier material, excipient, lubricant, buffer, antibacterial, bulking agent (such as mannitol), anti-oxidants (ascorbic acid of sodium bisulfate) or the like.

The dose administered may be carefully adjusted according to age, weight and condition of the patient, as well as the route of administration, dosage form and regimen and the desired result.

The compositions of the disclosure may be administered in the dosage forms in single or divided doses of one to four times daily, or may be administered multiple times per day. It may be advisable to start a patient on a low dose combination and work up gradually to a high dose combination.

Tablets of various sizes can be prepared, e.g., of about 2 to 2000 mg in total weight, containing one or both of the active ingredients, with the remainder being a physiologically acceptable carrier of other materials according to accepted practice. Gelatin capsules can be similarly formulated.

Liquid formulations can also be prepared by dissolving or suspending one or the combination of active substances in a conventional liquid vehicle acceptable for administration so as to provide the desired dosage in, for example, one to four teaspoonfuls.

Dosage forms can be administered to the patient on a regimen of, for example, one, two, three, four, five, six, or other multiple doses per day.

In order to more finely regulate the dosage schedule, the active substances may be administered separately in individual dosage units at the same time or carefully coordinated times. The respective substances can be individually formulated in separate unit dosage forms in a manner similar to that described above.

In formulating the compositions, the active substances, in the amounts described above, may be compounded according to accepted practice with a physiologically acceptable vehicle, carrier, excipient, binder, preservative, stabilizer, flavor, etc., in the particular type of unit dosage form.

Packaging/Treatment Kits

The present disclosure relates to a kit for conveniently and effectively carrying out the methods in accordance with the present disclosure. Such kits may be suited for the delivery of solid oral forms such as tablets or capsules. Such a kit may include a number of unit dosages. Such kits can include a means for containing the dosages oriented in the order of their intended use. An example of a means for containing the dosages in the order of their intended uses is a card. An example of such a kit is a "blister pack". Blister packs are well known in the packaging industry and are widely used for packaging unit dosage forms. If desired, the blister can be in the form of a childproof blister, i.e. a blister that is difficult for a child to open, yet can be readily opened by an adult. If desired, a memory aid can be provided, for example in the form of numbers, letters, or other markings or with a calendar feature and/or calendar insert, designating the days and the sections of a day in the treatment schedule in which the dosages can be administered, such as, for example, an AM dose is packaged with a "midday" and a PM dose; or an AM dose is packaged with a PM dose. Alternatively, placebo dosages, or vitamin or dietary supplements, either in a form similar to or distinct from the active dosages, can be included.

The disclosure provides compositions, including preparations, formulations and/or kits, comprising combinations of ingredients, as described above (including the multi-ingredient combinations of drugs of the disclosure), that are serviceable as therapies for treating, preventing or improving conditions, states and disease as provided in the disclosure. In one aspect, each member of the combination of ingredients is manufactured in a separate package, kit or container; or, all or a subset of the combinations of ingredients are manufactured in a separate package or container. In alternative aspects, the package, kit or container comprises a blister package, a clamshell, a tray, a shrink wrap and the like.

In one aspect, the package, kit or container comprises a "blister package" (also called a blister pack, or bubble pack). In one aspect, the blister package consists two or more separate compartments. This blister package is made up of two separate material elements: a transparent plastic cavity shaped to the product and its blister board backing. These two elements are then joined together with a heat sealing process which allows the product to be hung or displayed. Exemplary types of "blister packages" include: Face seal blister packages, gang run blister packages, mock blister packages, interactive blister packages, slide blister packages.

Blister packs, clamshells or trays are forms of packaging used for goods; thus, the disclosure provides for blister packs, clamshells or trays comprising a composition (e.g., a (the multi-ingredient combination of drugs of the disclosure) combination of active ingredients) of the disclosure. Blister packs, clamshells or trays can be designed to be non-reclosable, so consumers can tell if a package has already opened. They are used to package for sale goods where product tampering is a consideration, such as the agents of the disclosure. In one aspect, a blister pack of the disclosure comprises a moulded PVC base, with raised areas (the "blisters") to contain the tablets, pills, etc. comprising the combinations of the disclosure, covered by a foil laminate. Tablets, pills, etc. are removed from the pack either by peeling the foil back or by pushing the blister to force the tablet to break the foil. In one aspect, a specialized form of a blister pack is a strip pack.

In one aspect, a blister pack also comprises a method of packaging where the compositions comprising combinations of ingredients of the disclosure are contained in-between a card and clear PVC. The PVC can be transparent so the item (pill, tablet, geltab, etc.) can be seen and examined easily; and in one aspect, can be vacuum-formed around a mould so it can contain the item snugly and have room to be opened upon purchase. In one aspect, the card is brightly colored and designed depending on the item (pill, tablet, geltab, etc.) inside, and the PVC is affixed to the card using pre-formed tabs where the adhesive is placed. The adhesive can be strong enough so that the pack may hang on a peg, but weak enough so that this way one can tear open the join and access the item. Sometimes with large items or multiple enclosed pills, tablets, geltabs, etc., the card has a perforated window for access. In one aspect, more secure blister packs, e.g., for items such as pills, tablets, geltabs, etc. of the disclosure are used, and they can comprise of two vacuum-formed PVC sheets meshed together at the edges, with the informative card inside.

In one aspect, blister packaging comprises at least two components (e.g., is a multi-ingredient combination of drugs of the disclosure): a thermoformed "blister" which houses the product (e.g., a combination of the disclosure), and then a "blister card" that is a printed card with an adhesive coating on the front surface. During the assembly process, the blister component, which is most commonly made out of PVC, is attached to the blister card using a blister machine. Conventional blister packs can also be sealed.

As discussed herein, the products of manufacture of the disclosure can comprise the packaging of the therapeutic drug combinations of the disclosure, alone or in combination, as "blister packages" or as a plurality of packettes, including as lidded blister packages, lidded blister or blister card or packets, or a shrink wrap.

In one aspect, any of the disclosure's products of manufacture, including kits or blister packs, include memory aids to help remind patients when and how to take the agents of the disclosure.

The treatment kits can be constructed in a variety of forms familiar to one of ordinary skill in the art. The kits comprise at least one unit dosage of an active for administration according to a daily regimen and a means for containing the unit dosages. The treatment kits can, for example, be constructed for administration once daily, twice daily, thrice daily, four times daily, multiple administrations daily, or other dosage regimens. The kits comprise a means for the daily administration of an agent of the disclosure. In one embodiment the kits include from about one to about four unit dosages.

In one embodiment, the means for containing the unit dosages is a card, including, for example, a card that is capable of being folded. This card will be referred to herein as a main card, or alternatively a principal card or a first card, to distinguish it from additional optional cards, circulars, or other such materials which can be associated with the kit. This main card can be folded with a simple crease, or alternatively, with a double crease, so as to exhibit a spine, similar to the spine of a closed book. The main card can comprise a printable surface, i.e. a surface upon which the product name, appropriate administration instructions, product information, drawings, logos, memory aids, calendar features, etc. can be printed. The main card can comprise a means for containing said unit dosage or different dosages designated for different time of the day, and a memory aid for administering said unit dosage or dosages. The main card, especially if it is prepared from two or more laminated paperboard surfaces, can comprise a slit or pocket, for example in one of the inner paperboard surfaces of the folded card. The slit or pocket can be used to contain a removable secondary card, i.e. a second card or insert card, which is not permanently attached or affixed to the main card.

The memory aid can include a listing of the days of the week, i.e. Sunday, Monday, Tuesday, Wednesday, Thursday, Friday, and Saturday, with appropriate spaces for the patient to select and indicate on the card the preferred day of the week on which to administer the therapy. The memory aid can include a listing of the time of day with appropriate spaces for the patient to select and indicate on the card the preferred time of day (e.g.: AM, PM, midday) at which to administer the therapy. The memory aid can also include removable stickers having an appropriate pressure sensitive adhesive to facilitate easy removal and refastening to a desired surface such as a calendar or dayminder. The removable stickers can be located on the main card, or can be located on the secondary card which is constructed so that it can be readily inserted into and removed from the optional slit in the main card. Additionally, the optional slit can contain additional patient information and other circulars.

Other means for containing said unit dosages can include bottles and vials, wherein the bottle or vial comprises a memory aid, such as a printed label for administering said unit dosage or dosages. The label can also contain removable reminder stickers for placement on a calendar or dayminder to further help the patient to remember when to take a dosage or when a dosage has been taken.

The disclosure will be illustrated in more detail with reference to the following Examples, but it should be understood that the present disclosure is not deemed to be limited thereto.

EXAMPLES

Example 1

Colesevalam Hydrochloride Tablet 625 mg

| Ingredient | Qty/mg | % w/w |
|---|---|---|
| Colesevelam hydrochloride anhydrous | 625 | 63.13 |
| Microcrystalline cellulose (Avicel pH101) | 220 | 22.22 |
| Hydroxy propyl methylcellulose (HPMC E5LV) | 20 | 2 |
| Hydroxy propyl methylcellulose (K4M) | 100 | 10.1 |
| Colloidal silicon dioxide | 15 | 1.5 |
| Magnesium stearate | 10 | 1 |
| Core tablet weight | 990 | 100 |
| Coating | | |
| Hydroxypropyl methylcellulose (HPMC E50SLV) | 69.8 | 6.53 |
| Diacylated monoglyceride | 9.4 | 0.88 |
| water | q.s. | |
| Coated tablet total weight | 1069.2 | 100 |

Example 2

Colesevalam Hydrochloride Tablet 500 mg

| Ingredient | Qty/mg | % w/w |
|---|---|---|
| Colesevelam hydrochloride anhydrous | 500 | 57.8 |
| Microcrystalline cellulose (Avicel pH101) | 220 | 25.4 |
| Hydroxy propyl methylcellulose (HPMC E5LV) | 20 | 2.31 |
| Hydroxy propyl methylcellulose (K4M) | 100 | 11.56 |
| Colloidal silicon dioxide | 15 | 1.7 |
| Magnesium stearate | 10 | 1.16 |
| Core tablet weight | 865 | 100 |
| Coating | | |
| Hydroxypropyl methylcellulose (HPMC E50SLV) | 69.8 | 7.4 |
| Diacylated monoglyceride | 9.4 | 1 |
| Water | q.s. | |
| Coated tablet total weight | 944.2 | 100 |

Example 3

Colesevalam Hydrochloride Tablet 250 mg

| Ingredient | Qty/mg | % w/w |
|---|---|---|
| Colesevelam hydrochloride anhydrous | 250 | 40.65 |
| Microcrystalline cellulose (Avicel pH101) | 220 | 35.77 |
| Hydroxy propyl methylcellulose (HPMC E5LV) | 20 | 3.25 |
| Hydroxy propyl methylcellulose (K4M) | 100 | 16.26 |
| Colloidal silicon dioxide | 15 | 2.44 |
| Magnesium stearate | 10 | 1.6 |
| Core tablet weight | 615 | 100 |
| Coating | | |
| Hydroxypropyl methylcellulose (HPMC E50SLV) | 69.8 | 10.05 |
| Diacylated monoglyceride | 9.4 | 1.35 |
| Water | q.s. | |
| Coated tablet total weight | 694.2 | 100 |

Example 4

Colesevalam Hydrochloride Tablet 250 mg

| Ingredients | Qty/mg | % w/w |
|---|---|---|
| 1. Colesevalam Hydrochloride anhydrous | 250 | 57.5 |
| 2. Microcrystalline cellulose (Avicel pH101) | 110 | 25.28 |
| 3. Hydroxy propyl methylcellulose (HPMC E5LV) | 10 | 2.29 |
| 4. Hydroxy propyl methylcellulose (K4M) | 50 | 11.49 |
| 5. Colloidal silicon dioxide | 10 | 2.29 |
| 6. Magnesium stearate | 5 | 1.15 |
| 7. Core tablet weight | 435 | |
| Coating | | |
| 8. Hydroxypropyl methylcellulose (HPMC E50SLV) | 31.5 | 6.7 |
| 9. Diacylated monoglyceride | 3.5 | 0.74 |
| Water | q.s. | |
| 10. Coated tablet weight | 470 | |

Example 5

Colesevalam Hydrochloride Tablet 500 mg

| Ingredients | Qty/mg | % w/w |
|---|---|---|
| 1. Colesevalam Hydrochloride anhydrous | 500 | 57.8 |
| 2. Microcrystalline cellulose (Avicel pH101) | 220 | 25.43 |
| 3. Hydroxy propyl methylcellulose (HPMC E5LV) | 20 | 2.31 |
| 4. Hydroxy propyl methylcellulose (K4M) | 100 | 11.56 |
| 5. Colloidal silicon dioxide | 15 | 1.73 |
| 6. Magnesium stearate | 10 | 1.16 |
| 7. Core tablet weight | 865 | |
| Coating | | |
| 8. Hydroxypropyl methylcellulose (HPMC E50SLV) | 66.0 | 7.02 |
| 9. Diacylated monoglyceride | 9.0 | 0.96 |
| Water | q.s. | |
| 10. Coated tablet weight | 940 | |

Example 6

Colesevalam Hydrochloride Tablet 625 mg

| Ingredients | Qty/mg | % w/w |
|---|---|---|
| 1. Colesevalam Hydrochloride anhydrous | 625 | 63.13 |
| 2. Microcrystalline cellulose (Avicel pH101) | 220 | 22.22 |
| 3. Hydroxy propyl methylcellulose (HPMC E5LV) | 20 | 2.02 |
| 4. Hydroxy propyl methylcellulose (K4M) | 100 | 10.10 |
| 5. Colloidal silicon dioxide | 15 | 1.52 |
| 6. Magnesium stearate | 10 | 1.01 |
| 7. Core tablet weight | 990 | |
| Coating | | |
| 8. Hydroxypropyl methylcellulose (HPMC E50SLV) | 69.8 | 6.53 |
| 9. Diacylated monoglyceride | 9.4 | 0.88 |
| Water | q.s. | |
| 10. Coated tablet weight | 1069.2 | |

Example 7

Manufacturing Formula

Batch Size: 100000 Tablets

| S. No | Ingredients | mg/ tablet | % w/w per tablet | Qty./ Batch in kg |
|---|---|---|---|---|
| | Core Tablet | | | |
| 1 | Colesevalam Hydrochloride anhydrous | 625 | 63.13 | 62.5 |
| 2 | Microcrystalline cellulose (Avicel pH101) | 220 | 22.22 | 22.0 |
| 3 | Hydroxy propyl methylcellulose (HPMC E5LV) | 20 | 2.02 | 2.0 |
| 4 | Hydroxy propyl methylcellulose (K4M) | 100 | 10.10 | 10.0 |
| 5 | Colloidal silicon dioxide | 15 | 1.51 | 1.5 |
| 6 | Magnesium stearate | 10 | 1.01 | 1.0 |
| | Core tablet weight | 990 | | |
| | coating | | | |
| 7 | Hydroxypropyl methylcellulose (HPMC E50SLV) | 69.80 | 6.52 | 6.98 |
| 8 | Diacylated monoglyceride | 9.40 | 0.87 | 0.94 |
| 9 | P water | Q.S | — | Q.S |
| | Coated tablet weight | 1069.2 | — | — |

Manufacturing Process:

1. Sift colesevelam hydrochloride Microcrystalline cellulose, HPMC ES LV(R), Hydroxypropyl methyl cellulose (K4M(R) and Aerosil R-200 through 40imesh and mix for 10 minutes in bin blender. Sift Magnesium stearate through #60 mesh and add to the above blend and mix for another 5 min.

2. The above lubricated blend is then compressed into tablets Coating of Tablets.

3. Prepare coating solution by dissolving acetylated monoglyceride in purified water under stirring followed addition of HPMC E50LV(R) into it, under stirring until uniform dispersion formed.

4. The coating solution of 3) is sprayed onto the core tablets of 2) using a Suitable coating machine to achieve a weight gain between 6-8% w/w per tablet.

While the disclosure has been described in detail and with reference to specific examples thereof, it will be apparent to one skilled in the art that various changes and modifications can be made therein without departing from the spirit and scope thereof.

What is claimed is:

1. An oral drug delivery system comprising:
   a) a core comprising:
      a therapeutically effective amount of at least one active agent present in an amount of from about 50% to about 64% w/w of the core, wherein the at least one active agent is selected from the group consisting of colesevelam, pharmaceutically acceptable salts thereof, and combinations thereof, and
      a drug release controlling component capable of providing release of the at least one active agent primarily in a region of a patient selected from the group consisting of a lower gastrointestinal tract, a large intestine, a jejunum, a ileum, a cecum, a colon, a rectum, and combinations thereof,
      wherein the drug release controlling component comprises low viscosity hydroxypropyl methyl cellulose (HPMC) and high viscosity HPMC, and
      comprises at least one erodible matrix material selected from the group consisting of hydroxypropyl methylcellulose phthalate (HPMCP), hydroxypropylmethylcellulose acetate succinate (HPMCAS), hydroxypropyl methyl cellulose acetate trimellitate (HPMCAT), ethylhydroxy ethylcellulose (EHEC), and combinations thereof, wherein said at least one erodible matrix material is present in a concentration of about 5% to about 15% w/w of the core;
   b) a barrier coating encasing the core, wherein said barrier coating comprises HPMC, and
   c) an enteric coating on the barrier coating comprising hypromellose acetate succinate, and further comprising a plasticizer,
   wherein after ingestion by the patient the at least one active agent is released primarily in the region selected from the group consisting of the lower gastrointestinal tract, the large intestine, the jejunum, the ileum, the cecum, the colon, the rectum, and combinations thereof.

2. The system of claim 1, wherein the at least one active agent is present in an amount selected from the group consisting of about 250 mg, about 500 mg, about 625 mg, and about 650 mg.

3. The system of claim 1, wherein the at least one active agent is present in an amount of about 250 to about 650 mg.

4. The system of claim 1, wherein the at least one active agent is present in an amount of about 63.13% w/w of the core.

5. The system of claim 1, wherein the oral drug delivery system releases the at least one active agent primarily in the lower gastrointestinal tract.

6. The system of claim 1, wherein about 80% to about 100% w/w of the at least one active agent is released in the lower gastrointestinal tract.

7. The system of claim 1, wherein about 100% w/w of the at least one active agent is released in the lower gastrointestinal tract.

8. The system of claim 1, wherein the oral drug delivery system releases the at least one active agent primarily in the large intestine.

9. The system of claim 1, wherein about 80% to about 100% w/w of the at least one active agent is released in the large intestine.

10. The system of claim 1, wherein about 100% w/w of the at least one active agent is released in the large intestine.

11. The system of claim 1, wherein the oral drug delivery system releases the at least one active agent primarily in the colon.

12. The system of claim 1, wherein about 80% to about 100% w/w of the at least one active agent is released in the colon.

13. The system of claim 1, wherein about 100% w/w of the at least one active agent is released in the colon.

14. The system of claim 1, wherein the at least one erodible matrix material is present in a concentration of about 8% to about 13% w/w of the core.

15. The system of claim 1, wherein the at least one erodible matrix material is present in a concentration of about 12.12% w/w of the core.

16. The system of claim 1, wherein the core further comprises at least one excipient selected from the group consisting of: diluent, binding agent, lubricant, disintegrant, stabilizer, and combinations thereof.

17. The system of claim 1, wherein the core further comprises a disintegrant, wherein the disintegrant comprises colloidal silicon dioxide, in an amount of from about 0.1% to about 4% w/w of the core.

18. The system of claim 1, wherein the core further comprises a lubricant, wherein the lubricant comprises magnesium stearate, in an amount of from about 0.1% to about 4% w/w of the core.

19. The system of claim 1, wherein the enteric coating allows the at least one active agent to pass through a stomach substantially intact and subsequently disintegrate primarily in the large intestine of the patient.

20. The system of claim 1, wherein the plasticizer is present in a concentration of about 0.5% to about 2% w/w of the enteric coating.

21. The system of claim 1, wherein the plasticizer is present in a concentration of about 0.75% to about 1% w/w of the enteric coating.

22. The system of claim 1, wherein the plasticizer is present in a concentration of about 0.87% w/w of the enteric coating.

23. The system of claim 1, wherein the plasticizer is selected from the group consisting of dibutyl sebacate, diethyl phthalate, triethyl citrate, tributyl citrate, triacetin, acetylated monoglycerides, diacylated monoglyceride, phthalate esters, castor oil, and combinations thereof.

24. The system of claim 1, wherein the plasticizer is triethyl citrate.

* * * * *